US012599493B2

(12) United States Patent
Baker et al.

(10) Patent No.: US 12,599,493 B2
(45) Date of Patent: Apr. 14, 2026

(54) METHOD OF DEPLOYING AN INTRALUMINAL DEVICE AND INTRALUMINAL SYSTEM

(71) Applicant: BFKW, LLC, Johns Creek, GA (US)

(72) Inventors: Randal S. Baker, Grand Rapids, MI (US); Frederick J. Walburn, Johns Creek, GA (US)

(73) Assignee: BFKW, LLC, Johns Creek, GA (US)

( * ) Notice: Subject to any disclaimer, the term of this patent is extended or adjusted under 35 U.S.C. 154(b) by 559 days.

(21) Appl. No.: 18/116,676

(22) Filed: Mar. 2, 2023

(65) Prior Publication Data

US 2023/0277350 A1 Sep. 7, 2023

Related U.S. Application Data

(60) Provisional application No. 63/486,544, filed on Feb. 23, 2023, provisional application No. 63/385,700, (Continued)

(51) Int. Cl.
*A61F 5/00* (2006.01)

(52) U.S. Cl.
CPC ............ *A61F 5/0046* (2013.01); *A61F 5/003* (2013.01); *A61F 5/0043* (2013.01); *A61F 5/0089* (2013.01)

(58) Field of Classification Search
CPC .................... A61B 2018/00494; A61F 5/0069
See application file for complete search history.

(56) References Cited

U.S. PATENT DOCUMENTS 4,403,604 A 9/1983 Wilkinson et al.
4,607,618 A 8/1986 Angelchik
(Continued)

FOREIGN PATENT DOCUMENTS

CN 108938163 A 12/2018
EP 0760696 B1 8/2001
(Continued)

OTHER PUBLICATIONS

"Obesity: Super-Sized Medical Device Market", Start-Up, Mar. 2003, Technology Strategies (Long Article), pp. 1-10 and a cover page.

(Continued)

*Primary Examiner* — Adam Marcetich
*Assistant Examiner* — Ted Yang
(74) *Attorney, Agent, or Firm* — Gardner, Linn, Burkhart & Ondersma LLP

(57) ABSTRACT

A method of deploying an intraluminal device to the cardiac region of the stomach and an intraluminal system used to deploy an intraluminal device to the cardiac region of the stomach, wherein the intraluminal device has a wall defining a surface and an open portion of the surface that is adapted to be aligned with the gastroesophageal (GE) junction. The surface and the cardiac portion of the stomach are conformable with each other. The method includes deploying the intraluminal device trans-orally to the stomach with an endoscopic deployment device and retaining the device against the cardiac region of the stomach with the open portion generally aligned with the GE junction. The intraluminal device is fastened to the stomach from the abdominal cavity with at least one laparoscopic instrument while concurrently visualizing the device with an endoscope in the stomach while it is being fastened. The laparoscopic instrument is adapted to respond to the endoscope in order to adjust location between the laparoscopic instrument and intraluminal device while the laparoscopic instrument is fastening the intraluminal device.

18 Claims, 17 Drawing Sheets

Related U.S. Application Data filed on Dec. 1, 2022, provisional application No. 63/316,714, filed on Mar. 4, 2022.

(56) References Cited

U.S. PATENT DOCUMENTS

| | | | |
|---|---|---|---|
| 5,084,058 A * | 1/1992 | Li ..................... A61B 17/0469 606/139 | |
| 5,234,454 A | 8/1993 | Bangs | |
| 5,306,300 A | 4/1994 | Berry | |
| 5,366,504 A | 11/1994 | Andersen et al. | |
| 5,507,755 A | 4/1996 | Gresl et al. | |
| 5,662,713 A | 9/1997 | Andersen et al. | |
| 5,741,279 A | 4/1998 | Gordon et al. | |
| 5,820,584 A | 10/1998 | Crabb | |
| 6,146,416 A | 11/2000 | Andersen et al. | |
| 6,264,700 B1 | 7/2001 | Kilcoyne et al. | |
| 6,280,415 B1 | 8/2001 | Johnson | |
| 6,312,437 B1 | 11/2001 | Kortenbach | |
| 6,355,070 B1 | 3/2002 | Andersen et al. | |
| 6,398,802 B1 | 6/2002 | Yee | |
| 6,432,040 B1 | 8/2002 | Meah | |
| 6,447,533 B1 | 9/2002 | Adams | |
| 6,468,298 B1 | 10/2002 | Pelton | |
| 6,544,291 B2 | 4/2003 | Taylor | |
| 6,558,400 B2 | 5/2003 | Deem et al. | |
| 6,572,627 B2 | 6/2003 | Gabbay | |
| 6,656,194 B1 | 12/2003 | Gannoe et al. | |
| 6,675,809 B2 | 1/2004 | Stack et al. | |
| 6,736,828 B1 | 5/2004 | Adams et al. | |
| 6,740,121 B2 | 5/2004 | Geitz | |
| 6,746,460 B2 | 6/2004 | Gannoe et al. | |
| 6,755,869 B2 | 6/2004 | Geitz | |
| 6,773,440 B2 | 8/2004 | Gannoe et al. | |
| 6,800,081 B2 | 10/2004 | Parodi | |
| 6,802,868 B2 | 10/2004 | Silverman et al. | |
| 6,845,776 B2 | 1/2005 | Stack et al. | |
| 6,916,332 B2 | 7/2005 | Adams | |
| 6,960,233 B1 | 11/2005 | Berg et al. | |
| 6,981,978 B2 | 1/2006 | Gannoe | |
| 6,994,095 B2 | 2/2006 | Burnett | |
| 6,994,715 B2 | 2/2006 | Gannoe et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,044,979 B2 | 5/2006 | Silverman et al. | |
| 7,066,945 B2 | 6/2006 | Hashiba et al. | |
| 7,083,629 B2 | 8/2006 | Weller et al. | |
| 7,083,630 B2 | 8/2006 | DeVries et al. | |
| 7,087,088 B2 | 8/2006 | Berg et al. | |
| 7,097,650 B2 | 8/2006 | Weller et al. | |
| 7,097,665 B2 | 8/2006 | Stack et al. | |
| 7,111,627 B2 | 9/2006 | Stack et al. | |
| 7,146,984 B2 | 12/2006 | Stack et al. | |
| 7,152,607 B2 | 12/2006 | Stack et al. | |
| 7,167,750 B2 | 1/2007 | Knudson et al. | |
| 7,211,114 B2 | 5/2007 | Bessler et al. | |
| 7,220,284 B2 | 5/2007 | Kagan et al. | |
| 7,232,461 B2 | 6/2007 | Ramer | |
| 7,347,875 B2 | 3/2008 | Levine et al. | |
| 7,431,725 B2 | 10/2008 | Stack et al. | |
| 7,445,010 B2 | 11/2008 | Kugler et al. | |
| 7,449,024 B2 | 11/2008 | Stafford | |
| 7,678,068 B2 | 3/2010 | Levine et al. | |
| 7,682,330 B2 | 3/2010 | Meade et al. | |
| 7,704,264 B2 | 4/2010 | Ewers et al. | |
| 7,708,752 B2 | 5/2010 | Durgin | |
| 7,753,870 B2 | 7/2010 | Demarais et al. | |
| 7,771,382 B2 | 8/2010 | Levine et al. | |
| 7,794,447 B2 | 9/2010 | Dann et al. | |
| 7,815,589 B2 | 10/2010 | Meade et al. | |
| 7,815,591 B2 | 10/2010 | Levine et al. | |
| 7,846,174 B2 | 12/2010 | Baker et al. | |
| 7,922,650 B2 | 4/2011 | McWeeney et al. | |
| 7,976,488 B2 | 7/2011 | Levine et al. | |
| 7,981,163 B2 | 7/2011 | Meade et al. | |
| 8,029,455 B2 | 10/2011 | Stack et al. | |
| 8,043,355 B2 | 10/2011 | Shin et al. | |
| 8,100,931 B2 | 1/2012 | Baker et al. | |
| 8,137,301 B2 | 3/2012 | Levine et al. | |
| 8,142,513 B2 | 3/2012 | Shalon et al. | |
| 8,162,871 B2 | 4/2012 | Levine et al. | |
| 8,252,009 B2 | 8/2012 | Weller | |
| 8,282,598 B2 | 10/2012 | Belhe et al. | |
| 8,372,087 B2 | 2/2013 | Baker et al. | |
| 8,447,403 B2 | 5/2013 | Sharma et al. | |
| 8,506,477 B2 | 8/2013 | Waller et al. | |
| 8,529,431 B2 * | 9/2013 | Baker ................ A61B 17/0469 606/191 | |
| 8,556,956 B2 | 10/2013 | Cully et al. | |
| 8,672,831 B2 | 3/2014 | Baker et al. | |
| 8,721,528 B2 | 5/2014 | Ho et al. | |
| 8,778,011 B2 | 7/2014 | Ryan | |
| 8,784,436 B2 | 7/2014 | Ho et al. | |
| 8,801,599 B2 | 8/2014 | Baker et al. | |
| 8,894,670 B2 * | 11/2014 | Baker ................... A61F 5/0076 606/153 | |
| 9,055,998 B2 | 6/2015 | Baker | |
| 9,060,844 B2 | 6/2015 | Kagan et al. | |
| 9,107,742 B2 | 8/2015 | Cully et al. | |
| 9,198,789 B2 | 12/2015 | Baker et al. | |
| 9,375,338 B2 | 6/2016 | Baker et al. | |
| 9,414,948 B2 | 8/2016 | Baker et al. | |
| 9,545,326 B2 | 1/2017 | Baker et al. | |
| 9,549,833 B2 | 1/2017 | McHugo | |
| 9,629,733 B2 | 4/2017 | Roeder | |
| 9,839,545 B2 | 12/2017 | Baker et al. | |
| 9,872,787 B2 | 1/2018 | Baker et al. | |
| 10,182,901 B2 | 1/2019 | Baker et al. | |
| 10,271,940 B2 | 4/2019 | Baker et al. | |
| 10,682,219 B2 | 6/2020 | Foote et al. | |
| 10,687,933 B2 | 6/2020 | Baker et al. | |
| 10,786,380 B2 | 9/2020 | Baker et al. | |
| 10,792,174 B2 | 10/2020 | Baker et al. | |
| 11,013,629 B2 * | 5/2021 | Baker ................... A61F 5/0089 | |
| 11,020,213 B2 | 6/2021 | Foote et al. | |
| 11,129,703 B2 | 9/2021 | Baker et al. | |
| 2001/0011543 A1 | 8/2001 | Forsell | |
| 2001/0020189 A1 | 9/2001 | Taylor | |
| 2002/0032487 A1 | 3/2002 | Dua et al. | |
| 2002/0055757 A1 | 5/2002 | Torre et al. | |
| 2002/0091395 A1 | 7/2002 | Gabbay | |
| 2003/0040804 A1 | 2/2003 | Stack et al. | |
| 2003/0040808 A1 | 2/2003 | Stack et al. | |
| 2003/0065359 A1 | 4/2003 | Weller et al. | |
| 2003/0109935 A1 | 6/2003 | Geitz | |
| 2003/0199989 A1 | 10/2003 | Stack et al. | |
| 2003/0212450 A1 | 11/2003 | Schlick | |
| 2004/0044357 A1 | 3/2004 | Gannoe et al. | |
| 2004/0087976 A1 | 5/2004 | DeVries et al. | |
| 2004/0092892 A1 * | 5/2004 | Kagan ................ A61B 17/0401 604/270 | |
| 2004/0106987 A1 | 6/2004 | Palasis et al. | |
| 2004/0116999 A1 | 6/2004 | Ledergerber | |
| 2004/0117031 A1 | 6/2004 | Stack et al. | |
| 2004/0122456 A1 | 6/2004 | Vahid | |
| 2004/0138761 A1 | 7/2004 | Stack et al. | |
| 2004/0143342 A1 | 7/2004 | Stack et al. | |
| 2004/0148034 A1 | 7/2004 | Kagan et al. | |
| 2004/0153167 A1 | 8/2004 | Stack et al. | |
| 2004/0172141 A1 | 9/2004 | Stack et al. | |
| 2004/0210111 A1 | 10/2004 | Okada | |
| 2004/0220682 A1 | 11/2004 | Levine et al. | |
| 2005/0004582 A1 | 1/2005 | Edoga et al. | |
| 2005/0043683 A1 | 2/2005 | Ravo | |
| 2005/0080395 A1 | 4/2005 | Levine et al. | |
| 2005/0096673 A1 * | 5/2005 | Stack ................. A61B 17/0469 606/151 | |
| 2005/0096728 A1 | 5/2005 | Ramer | |
| 2005/0119674 A1 * | 6/2005 | Gingras ................ A61F 5/0086 606/151 | |
| 2005/0125020 A1 | 6/2005 | Meade et al. | |
| 2005/0177181 A1 | 8/2005 | Kagan | |
| 2005/0192599 A1 | 9/2005 | Demarais | |

(56) References Cited

U.S. PATENT DOCUMENTS

| | | | |
|---|---|---|---|
| 2005/0192629 A1 | 9/2005 | Saadat et al. | |
| 2005/0197715 A1 | 9/2005 | Kugler et al. | |
| 2005/0203548 A1 | 9/2005 | Weller et al. | |
| 2005/0228504 A1 | 10/2005 | Demarais | |
| 2005/0245788 A1 | 11/2005 | Gerber | |
| 2005/0245957 A1 | 11/2005 | Starkebaum et al. | |
| 2005/0247320 A1 | 11/2005 | Stack et al. | |
| 2005/0251165 A1 | 11/2005 | Vaughan et al. | |
| 2005/0251176 A1 | 11/2005 | Swanstrom et al. | |
| 2005/0283235 A1 | 12/2005 | Kugler et al. | |
| 2006/0020247 A1 | 1/2006 | Kagan et al. | |
| 2006/0020277 A1 | 1/2006 | Gostout et al. | |
| 2006/0036293 A1 | 2/2006 | Whitehurst et al. | |
| 2006/0064120 A1 | 3/2006 | Levine et al. | |
| 2006/0074473 A1 | 4/2006 | Gertner | |
| 2006/0089571 A1 | 4/2006 | Gertner | |
| 2006/0142844 A1 | 6/2006 | Lowe et al. | |
| 2006/0149307 A1 | 7/2006 | Durgin | |
| 2006/0155375 A1 | 7/2006 | Kagan et al. | |
| 2006/0161139 A1 | 7/2006 | Levine et al. | |
| 2006/0190019 A1 | 8/2006 | Gannoe et al. | |
| 2006/0240096 A1* | 10/2006 | Kugler | A61K 9/0009 |
| | | | 604/20 |
| 2006/0247721 A1 | 11/2006 | Maschino et al. | |
| 2006/0253131 A1 | 11/2006 | Wolniewicz, III | |
| 2006/0253142 A1 | 11/2006 | Bjerken | |
| 2006/0253191 A1 | 11/2006 | Salahieh et al. | |
| 2006/0264699 A1 | 11/2006 | Gertner | |
| 2006/0265082 A1 | 11/2006 | Meade et al. | |
| 2007/0005147 A1 | 1/2007 | Levine et al. | |
| 2007/0010866 A1 | 1/2007 | Dann et al. | |
| 2007/0010875 A1 | 1/2007 | Trout et al. | |
| 2007/0088428 A1 | 4/2007 | Teichman | |
| 2007/0112409 A1 | 5/2007 | Wu et al. | |
| 2007/0123994 A1 | 5/2007 | Ortiz et al. | |
| 2007/0166396 A1 | 7/2007 | Badylak et al. | |
| 2007/0179590 A1 | 8/2007 | Lu et al. | |
| 2007/0198035 A1 | 8/2007 | Threlkeld | |
| 2007/0208360 A1 | 9/2007 | Demarais et al. | |
| 2007/0208429 A1 | 9/2007 | Leahy | |
| 2007/0233221 A1 | 10/2007 | Raju | |
| 2007/0260112 A1 | 11/2007 | Rahmani | |
| 2007/0270742 A1 | 11/2007 | Guetty | |
| 2007/0276432 A1 | 11/2007 | Stack et al. | |
| 2007/0293716 A1* | 12/2007 | Baker | A61F 5/0089 |
| | | | 600/37 |
| 2008/0015523 A1* | 1/2008 | Baker | A61J 15/0084 |
| | | | 604/288.01 |
| 2008/0015618 A1 | 1/2008 | Sonnenschein et al. | |
| 2008/0015633 A1 | 1/2008 | Abbott et al. | |
| 2008/0065122 A1 | 3/2008 | Stack et al. | |
| 2008/0065136 A1 | 3/2008 | Young | |
| 2008/0215076 A1* | 9/2008 | Baker | A61B 17/1114 |
| | | | 606/154 |
| 2008/0249474 A1* | 10/2008 | Baker | A61B 17/3423 |
| | | | 606/191 |
| 2008/0312678 A1 | 12/2008 | Pasricha | |
| 2009/0018389 A1 | 1/2009 | Laufer et al. | |
| 2009/0138071 A1 | 5/2009 | Cheng et al. | |
| 2009/0177215 A1 | 7/2009 | Stack et al. | |
| 2009/0187230 A1 | 7/2009 | Dilorenzo | |
| 2009/0240340 A1 | 9/2009 | Levine et al. | |
| 2009/0248171 A1 | 10/2009 | Levine et al. | |
| 2009/0270818 A1 | 10/2009 | Duke | |
| 2010/0010298 A1 | 1/2010 | Bakos et al. | |
| 2010/0030017 A1* | 2/2010 | Baker | A61B 17/0401 |
| | | | 600/37 |
| 2010/0063518 A1* | 3/2010 | Baker | A61B 17/062 |
| | | | 606/144 |
| 2010/0114130 A1 | 5/2010 | Meade et al. | |
| 2010/0198237 A1* | 8/2010 | Baker | A61F 5/0079 |
| | | | 606/153 |
| 2010/0256775 A1 | 10/2010 | Belhe et al. | |
| 2010/0280313 A1 | 11/2010 | Gasche et al. | |

| | | | |
|---|---|---|---|
| 2010/0305590 A1 | 12/2010 | Holmes et al. | |
| 2011/0004146 A1 | 1/2011 | Priplata et al. | |
| 2011/0009690 A1 | 1/2011 | Belhe et al. | |
| 2011/0264234 A1* | 10/2011 | Baker | A61F 2/04 |
| | | | 623/23.64 |
| 2012/0053653 A1 | 3/2012 | Hiernaux et al. | |
| 2012/0083871 A1 | 4/2012 | Ryan | |
| 2012/0095497 A1 | 4/2012 | Babkes et al. | |
| 2012/0191213 A1 | 7/2012 | Baker et al. | |
| 2012/0191215 A1 | 7/2012 | Baker et al. | |
| 2012/0203061 A1 | 8/2012 | Birk | |
| 2012/0232361 A1* | 9/2012 | Birk | A61B 5/037 |
| | | | 600/300 |
| 2012/0289991 A1* | 11/2012 | Baker | A61F 5/0013 |
| | | | 606/191 |
| 2013/0123811 A1 | 5/2013 | Baker et al. | |
| 2013/0296913 A1* | 11/2013 | Foote | A61F 2/04 |
| | | | 606/191 |
| 2013/0310327 A1 | 11/2013 | Sambursky et al. | |
| 2013/0324902 A1 | 12/2013 | Miller et al. | |
| 2013/0331642 A1* | 12/2013 | Schauer | A61F 5/0063 |
| | | | 600/37 |
| 2014/0039278 A1* | 2/2014 | Birk | A61B 5/42 |
| | | | 600/300 |
| 2014/0121585 A1* | 5/2014 | Baker | A61F 2/04 |
| | | | 604/9 |
| 2014/0135799 A1 | 5/2014 | Henderson | |
| 2014/0158747 A1 | 6/2014 | Measamer et al. | |
| 2014/0277341 A1 | 9/2014 | Havel et al. | |
| 2015/0025313 A1* | 1/2015 | Baker | A61F 5/0079 |
| | | | 600/104 |
| 2015/0182239 A1* | 7/2015 | Baker | A61B 1/00148 |
| | | | 606/115 |
| 2016/0151233 A1* | 6/2016 | Baker | A61F 2/04 |
| | | | 601/148 |
| 2016/0228268 A1 | 8/2016 | Hingston et al. | |
| 2017/0000638 A1* | 1/2017 | Zeiner | A61F 5/0076 |
| 2017/0055986 A1* | 3/2017 | Harris | A61M 37/00 |
| 2017/0172723 A1 | 6/2017 | Foote et al. | |
| 2017/0360550 A1* | 12/2017 | Foote | A61F 5/0089 |
| 2018/0235794 A1 | 8/2018 | Kagan et al. | |
| 2019/0038394 A1* | 2/2019 | Foote | A61F 2/04 |
| 2019/0262156 A1* | 8/2019 | Baker | A61B 17/068 |
| 2019/0298560 A1 | 10/2019 | Belhe et al. | |
| 2020/0276007 A1* | 9/2020 | Musara | A61F 2/0063 |
| 2020/0390579 A1 | 12/2020 | Baker et al. | |

FOREIGN PATENT DOCUMENTS

| | | |
|---|---|---|
| EP | 1808888 A2 | 7/2007 |
| EP | 2240215 B1 | 1/2014 |
| JP | 2660101 | 6/1997 |
| JP | 2006-103873 A | 4/2006 |
| JP | 2007508053 A | 4/2007 |
| JP | 2011509758 A | 3/2011 |
| RU | 2045233 C1 | 10/1995 |
| RU | 94026119 A | 8/1996 |
| RU | 2386455 | 4/2010 |
| WO | WO 93/22986 | 11/1993 |
| WO | WO 94/12136 | 6/1994 |
| WO | WO 01/35834 A1 | 5/2001 |
| WO | WO 01/85034 A1 | 11/2001 |
| WO | WO 02/060328 A1 | 8/2002 |
| WO | WO 02/094105 A2 | 11/2002 |
| WO | WO 2004/019826 A1 | 3/2004 |
| WO | WO 2004/064680 A1 | 8/2004 |
| WO | WO 2004/064685 | 8/2004 |
| WO | WO 2005/037152 A1 | 4/2005 |
| WO | WO 2006/044640 A1 | 4/2006 |
| WO | WO 2006/078672 A1 | 7/2006 |
| WO | WO 2007/092390 A2 | 8/2007 |
| WO | WO 2008/100984 A2 | 8/2008 |
| WO | WO 2008/101048 A2 | 8/2008 |
| WO | WO 2008/101078 A2 | 8/2008 |
| WO | WO 2009/048398 A1 | 4/2009 |
| WO | WO 2009/091899 A2 | 7/2009 |
| WO | WO 2010/117641 A2 | 10/2010 |
| WO | WO 2011/056608 A1 | 5/2011 |

(56) References Cited

FOREIGN PATENT DOCUMENTS

| WO | WO 2011/063307 A1 | 5/2011 |
| WO | WO 2011/089601 A1 | 7/2011 |
| WO | WO 2011/097209 A1 | 8/2011 |
| WO | WO 2011/116025 A1 | 9/2011 |
| WO | WO 2012/044917 A1 | 4/2012 |
| WO | WO 2012/136249 A1 | 10/2012 |
| WO | WO 2012/162114 A1 | 11/2012 |
| WO | WO 2013/090190 A1 | 6/2013 |
| WO | WO 2013/134227 A1 | 9/2013 |
| WO | WO 2014/141239 A1 | 9/2014 |
| WO | WO 2015/031077 A1 | 3/2015 |
| WO | WO 2016/109346 A1 | 7/2016 |
| WO | WO 2018/073752 A1 | 4/2018 |
| WO | WO 2018/083632 A1 | 5/2018 |
| WO | 2020183399 A1 | 9/2020 |

OTHER PUBLICATIONS

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, three pages (2003).

Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism , pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Summary of Official Action dated Oct. 29, 2009, from the Israel Patent Office in a patent application corresponding to the present application.

Lowe, Andrew S., M.D. and Sheridan, Maria B., M.D., "Esophageal Stenting," annotated by Israel Patent Office (2004).

Abstract and claims of U.S. Pat. No. 6,960,233 annotated by the Israel Patent Office (Nov. 1, 2005).

Schembre, Drew, "Advances in Esophageal Stenting: the Evolution of Fully Covered Stents for Malignant and Benign Disease," Adv. Ther., Springer Healthcare, Apr. 1, 2010, pp. 1-13.

S. Fukudo, T. Nomura, M. Hongo, "Impact of corticotropin-releasing hormone on gastrointestinal motility and adrenocorticotropic hormone in normal controls and patients with irritable bowl syndrome", Jan. 19, 1998.

D.G. Maxton, D.F. Martin, P.J. Whorwell, M. Godfrey. "Abdominal distension in female patients with irritable bowel syndrome: exploration of possible mechanisms", Aug. 3, 1990.

Dixon et al. "Health Outcomes of Severely Obese Type 2 Diabetic Subjects 1 Year After Laparoscopic Adjustable Gastric Banding". 2002. Diabetic Care 25:358-363. (Year 2002).

Fried, M., G Ribaric, J. N. Buchwald, S. Svacina, K. Dolezalova, N. Scopinaro. "Metabolic Surgery for the Treatment of Type 2 Diabetes in Patients with BMI <35 kg/m²: An Integrative Review of Early Studies". (2010). Obesity Surgery 20:776-790. (Year 2010).

International Search Report and Written Opinion from corresponding Patent Cooperation Treaty (PCT) Application No. PCT/IB23/51970, completed May 1, 2023.

* cited by examiner

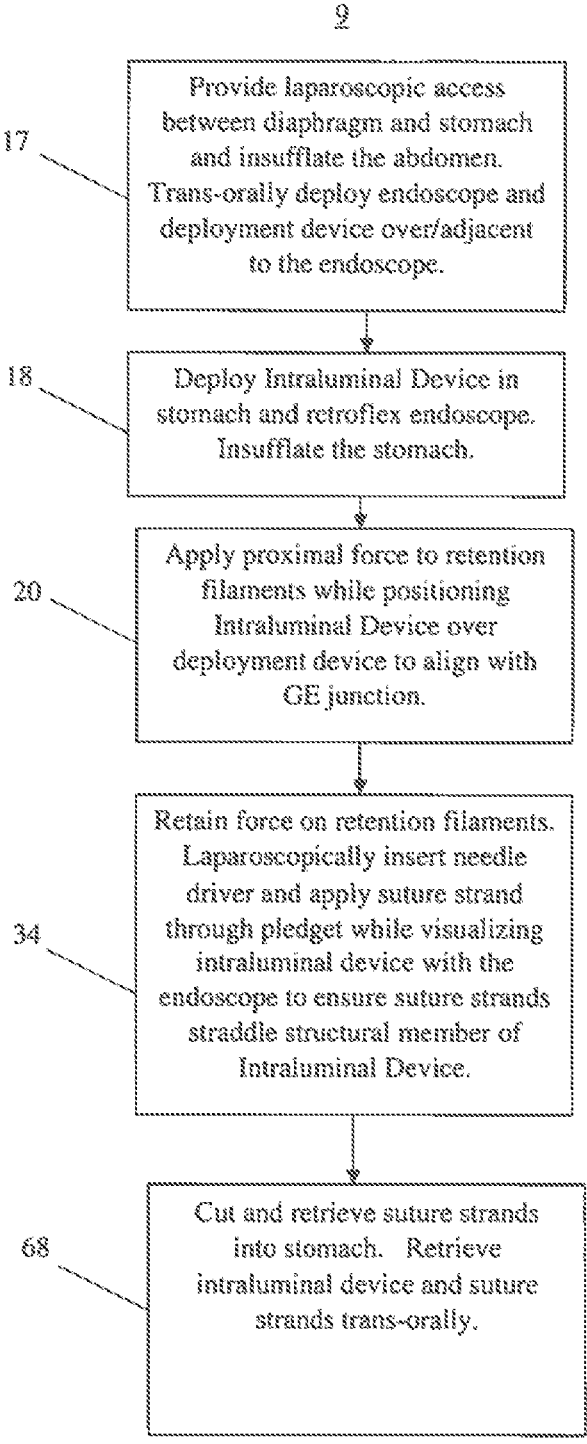

9

Provide laparoscopic access
between diaphragm and stomach
and insufflate the abdomen.
Trans-orally deploy endoscope and
deployment device over/adjacent
to the endoscope.

17

Deploy Intraluminal Device in
stomach and retroflex endoscope.
Insufflate the stomach.

18

Apply proximal force to retention
filaments while positioning
Intraluminal Device over
deployment device to align with
GE junction.

20

Retain force on retention filaments.
Laparoscopically insert needle
driver and apply suture strand
through pledget while visualizing
intraluminal device with the
endoscope to ensure suture strands
straddle structural member of
Intraluminal Device.

34

Cut and retrieve suture strands
into stomach.   Retrieve
intraluminal device and suture
strands trans-orally.

Robot
Controller — 402

Esophogeal
Robotic
Portion — 404

Abdominal
Robotic
Portion — 406

METHOD OF DEPLOYING AN INTRALUMINAL DEVICE AND INTRALUMINAL SYSTEM

CROSS REFERENCE TO RELATED APPLICATION

The present application claims the benefit of U.S. provisional application Ser. No. 63/316,714, filed Mar. 4, 2022; and U.S. provisional application Ser. No. 63/385,700, filed Dec. 1, 2022; and U.S. provisional application Ser. No. 63/486,544, filed Feb. 23, 2023, which are hereby incorporated herein by reference in their entireties.

BACKGROUND OF THE INVENTION

The present invention is directed to a method and system for deploying and anchoring an intraluminal device in a manner that applies stress to the cardiac portion of the stomach.

SUMMARY OF THE INVENTION

A method of deploying an intraluminal device to the cardiac region of the stomach, according to an aspect of the invention, includes having an intraluminal device with a wall defining a surface and an open portion of the wall that is alignable with the gastroesophageal (GE) junction. The surface and the cardiac portion of the stomach are conformable with each other. The intraluminal device is deployed trans-orally to the stomach. The intraluminal device is retained in contact with the cardiac region of the stomach with the open portion generally aligned with the GE junction. The intraluminal device is fastened from the abdominal cavity with at least one laparoscopic instrument. The intraluminal device is visualized with an endoscope while it is being fastened in order to guide the laparoscopic instrument.

The intraluminal device may be deployed from a deployment device in the stomach and the intraluminal device retained including by positioning the release device within the opening in the wall in order to generally align the opening with the GE junction. The intraluminal device may further be retained by applying a proximal force on at least one retention filament connected with the wall and passing the retention filament through the esophagus. The wall may have a mean radius measured from the open portion and wherein the fastening is within a half of the radius closest to said open portion. The fastening may be within a third of the radius closest to the open portion or within a quarter of the radius closest to the open portion.

The intraluminal device may be sutured with suture strands and the suture strands reinforced at the abdominal side of each suture strand. The strands may be reinforced by providing radial restraint to the suture strands. The radial restraint of the strands may include engaging adjacent suture strands with each other. The reinforcing may include producing scar material in the stomach tissue contacted by the suture strand. The scar material may be produced by positioning a biologically absorbable material, such as a pledget between the suture strand and the stomach tissue. The suture stands may be made from a non-absorbable material. While the knot of the suture strand may be retracted to the stomach through the scar material to explant the intraluminal device after use, such knot material would not be retractable should non-absorbable reinforcing material had been used for reinforcement in the abdominal cavity.

The biologically absorbable material may include multiple layers, each having a different rate of absorption. The layer with a highest rate of absorption may be positioned against the stomach wall. The layer furthest from the stomach tissue may have an outer surface that is adapted to resist adhering to another surface. Alternatively, or in addition, the reinforcing member may include a structural component that resists warping. The intraluminal device may be explanted by severing the suture strands in the stomach and pulling the knots of the severed suture strands through the stomach wall into the stomach.

The intraluminal device wall may include at least one structural member and the suturing includes straddling the at least one structural member with the suture strands. The intraluminal device may be explanted by severing the suture strands at the at least one structural member and pulling the suture strands through the stomach wall into the stomach. The intraluminal device may be explanted by severing the suture strands in the stomach and pulling the knots of the severed suture strands through the stomach wall into the stomach. The intraluminal device may have a plurality of structural members and have a higher density of the structural members proximal the opening than distal the opening.

The stress applied to the cardiac portion of the stomach with said intraluminal device may be adjustable. The applied stress may be adjustable with a controller affixed with the wall of the intraluminal device. The applied stress may be adjustable by varying an amount of contact between the intraluminal device wall and the stomach wall. The applied stress may be adjusted with at least one bladder that is connected with an external port.

The intraluminal device may be made at least in part from a bio-absorbable material. The wall of the intraluminal device may include an involute collar around the opening. The fastening may include having at least one magnet on either the wall of the intraluminal device engaging or in the abdominal cavity of the patient magnetically attracting a metallic member on the other of the wall or the abdominal cavity. The fastening may be using various forms of fasteners inserted with the laparoscopic device.

The intraluminal device may be used as a bariatric device or to treat a metabolic disease. The intraluminal device may be used to treat reflux disease or to treat hiatal hernia. The intraluminal device may be explanted by severing the sutures in the stomach and retracting the severed suture strands into the stomach including pulling the knots through the stomach wall and removing the intraluminal device and suture strands through the esophagus.

An intraluminal system that is adapted to deploy an intraluminal device to the cardiac region of the stomach, according to an aspect of the invention, includes an intraluminal device having a wall defining a surface and an opening in said surface that is alignable with the gastroesophageal (GE) junction. The surface and the cardiac portion of the stomach are conformable with each other. The system includes an endoscopic deployment device that is adapted to deploying the intraluminal device trans-orally to the stomach and an endoscope and a laparoscopic instrument. The endoscope is adapted to visualize the intraluminal device in the stomach while the intraluminal device is being fastened to the cardiac portion of the stomach. The laparoscopic instrument is adapted to fasten the intraluminal device to the cardiac portion of the stomach from within the abdominal cavity while guided by the visualization of the intraluminal device by the endoscope. The laparoscopic instrument is adapted to respond to the endoscope in order to adjust relative location between the laparoscopic instrument and the intraluminal device while the laparoscopic instrument is fastening the intraluminal device.

The deployment device may be a combination endoscope and deployment device defined by the intraluminal device positioned at an exterior surface of said endoscope. The endoscope may include a shaft having a distal end portion that is adapted to be retroflexed and the intraluminal device is positioned proximal of the distal end portion. The intraluminal device may have a self-expandable wall that is compressed to the endoscope shaft. A compression device may be provided having a sleeve or a wrapped filament over the intraluminal device to keep the wall compressed to the endoscope. A deploying filament may be provided to extend external the patient to release the compression device to allow the intraluminal device to self-expand in the patient's stomach.

One or more filament guides may be provided positioned on the endoscope shaft proximal the intraluminal device and adapted to guide movement of the deploying filament. Alternatively, the deploying filament may extend external the patient through a working channel of the endoscope.

A kit that is adapted for use with an endoscope having a shaft to convert the endoscope into a combination endoscope and intraluminal device release device, according to an aspect of the invention, includes a holder having an inner diameter that is larger than an external diameter of the endoscope shaft. An intraluminal device having a self-expandable wall is positioned on the holder. A compression device made up of a sleeve or a wrapped filament over the intraluminal device keeps the wall compressed to the holder. A deploying filament extending external the patient, to release the compression device to allow the intraluminal device to self-expand.

One or more filament guides may be positioned on the holder and adapted to guide movement of the deploying filament when positioned on the endoscope shaft.

The holder may be adapted to receive the one or more filament guides and compression device after use of the combination endoscope and intraluminal device.

A method of converting an endoscope to a combination endoscope and intraluminal device release device using such a kit, according to an aspect of the invention, includes positioning the holder over the endoscope shaft and positioning the intraluminal device and compression device to the shaft by moving the intraluminal device and compression device from the holder to the endoscope shaft.

The endoscope may include a distal end portion that is adapted to be retroflexed and the method including positioning the intraluminal device and compression device proximal of the distal end portion. One or more filament guides may be provided on the holder proximal to the intraluminal device and compression device and the method further including positioning the filament guide(s) on the endoscope shaft by moving filament guide(s) from the holder to the endoscope shaft before positioning the intraluminal device and compression device to the shaft. The holder may be slid distally after moving each filament guide from the holder to the endoscope shaft and before moving the intraluminal device and compression device from the holder to the endoscope shaft.

The invention provides a minimally invasive technique for securely affixing an intraluminal device using mostly common surgical tools. This can be accomplished endoscopically and laparoscopically. The intraluminal device can be easily explanted after use and, if the intraluminal device experiences distal migration, it will reside harmlessly in the stomach where it can be endoscopically retrieved or reaffixed. The positioning of the intraluminal device against the cardiac portion of the stomach may simulate a sensation of fullness in the patient's stomach in the absence of food or supplement fullness from the presence of food, using a variety of techniques. Pressure, or stress applied to the stomach wall may engage barro or stretch receptors in the stomach wall. Peristalsis in the stomach wall may also create a sense of fullness by causing relative movement between the stomach wall and the wall of the intraluminal device thus activating the barro receptors. Activating of the barro receptors may cause neurohormonal change in the patient and trigger brain activity to affect satiety. The intraluminal device performs its function without restricting any portion of the esophagus or encroaching upon the GE junction.

An intraluminal system that is adapted to deploy an intraluminal device to the cardiac region of the stomach, according to an aspect of the invention, includes an intraluminal device comprising a wall defining a surface and an open portion of the surface that is alignable with the gastroesophageal (GE) junction. The surface and the cardiac portion of the stomach are conformable with each other. An endoscopic release device is adapted to deploying the intraluminal device trans-orally to the stomach. An endoscope is adapted to visualize the intraluminal device in the stomach while the intraluminal device is being fastened to the cardiac portion of the stomach. A laparoscopic instrument is adapted to fasten the intraluminal device to the cardiac portion of the stomach from within the abdominal cavity while guided based upon information gained from visualization of the intraluminal device during the fastening.

The deployment device, according to an aspect of the invention, is the endoscope with the intraluminal device positioned at an exterior surface of the endoscope. Such combination of deployment device and visualization device eliminates one of the instruments deployed trans-orally in the patient. Since the endoscope does not need to fit through the center of a deployment device, a larger endoscope shaft diameter may be used while still fitting through the esophagus. Better visualization may be achieved with a larger diameter endoscope. Also, only a conversion kit as disclosed herein, may be supplied and used to convert a conventional endoscope to a combination endoscope and deployment device. This reduces material usage and should lessen regulatory approval. Also, a disposable combination device may be provided that can be supplied in a single sterile package and disposed of after the procedure.

These and other objects, advantages, purposes and features of this invention will become apparent upon review of the following specification in conjunction with the drawings.

BRIEF DESCRIPTION OF THE DRAWINGS

FIG. 11 is a block diagram of a method of deploying an intraluminal device according to an aspect of the invention;

DESCRIPTION OF THE PREFERRED EMBODIMENTS

Figure 1:
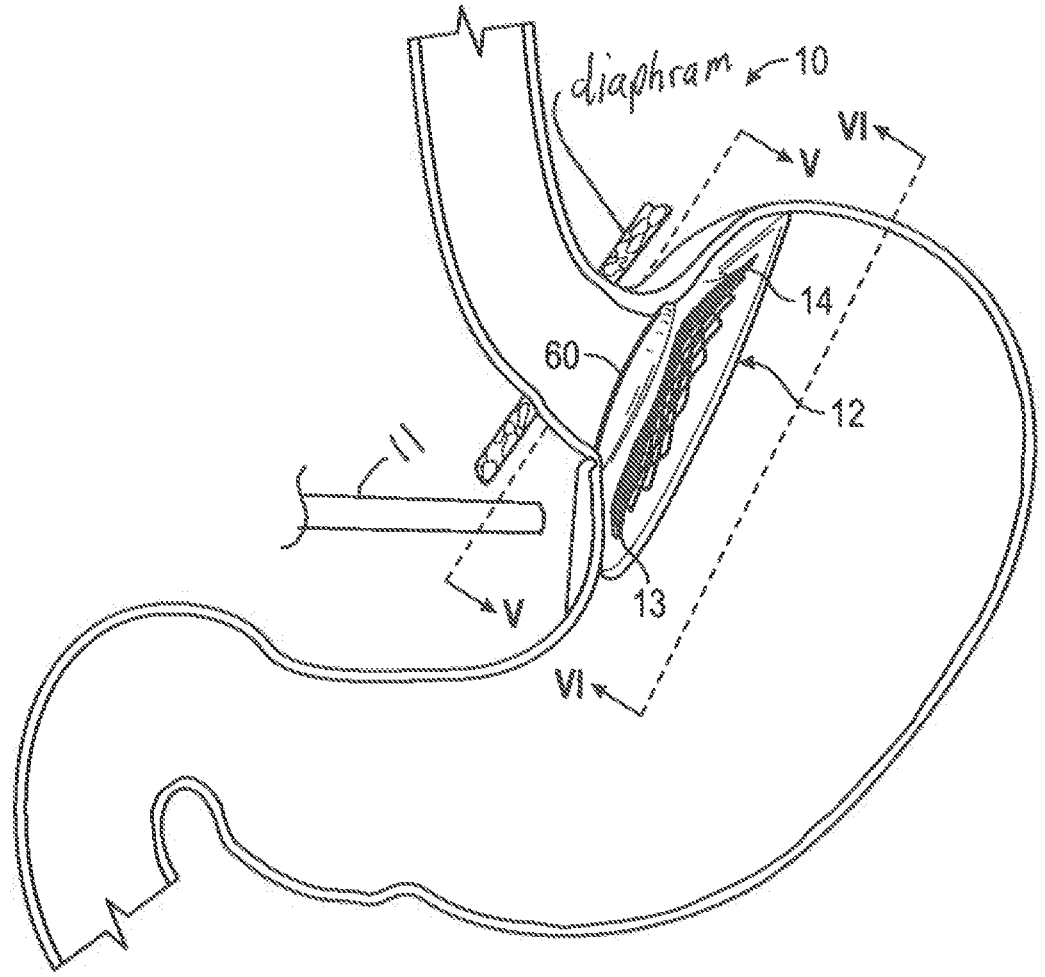
FIG. 1 is a perspective view of an intraluminal device deployed to a patient according to an embodiment of the invention.

The present invention will now be described with reference to the accompanying figures, wherein the numbered elements in the following written description correspond to like-numbered elements in the figures. A method 9 is provided for deploying an intraluminal device 10 to the cardiac region of the stomach. The intraluminal device 10 includes a wall 12 defining a surface 14 providing an open portion 16 that is alienable with the gastroesophageal (GE) junction of the patient. While open portion 16 is a generally central, through opening in wall 12 it could alternatively be a notch or other shape depending on the configuration of the intraluminal device. Wall 12 and the cardiac portion of the stomach are conformable to each other in order to stimulate baroreceptors in the wall of the cardiac portion of the stomach. This may be accomplished by the fastening of wall 12 to the stomach wall bringing the device wall and the stomach wall into physical contact in order to apply stress to the wall of the stomach. Alternatively, device wall 12 and the stomach wall may be more loosely joined so that the peristalsis of the stomach will bring the stomach wall into engagement will the device wall to stimulate baroreceptors. Detail operation of intraluminal device 10 is described in U.S. Pat. No. 7,846,174 and Patent Application Publication US 2016/0151233, the disclosures of which are hereby incorporated herein by reference in their entirely.

Wall 12 is constructed of a structural element 13 and a flexible membrane 15 between loops of the structural element. Structural element 13 can be made from any suitable material that can provide rigidity but be flexible, such as a metal such as nitinol, or a polymeric material or carbon filament of the type known in the art. Structure element 13 may take various shapes such as seen in FIGS. 6, 8A-8E and 10 in order to provide enough rigidity to wall 12 to apply suitable stress to the cardiac portion of the stomach without concentrating stress at particular locations. Yet, wall 12 is flexible enough to be able to be compressed to a deployment device 24. Flexible membrane 15 can be made from a biocompatible material such as silicone, or the like, and of a suitable thickness to provide rigidity but be flexible.

Figure 2:
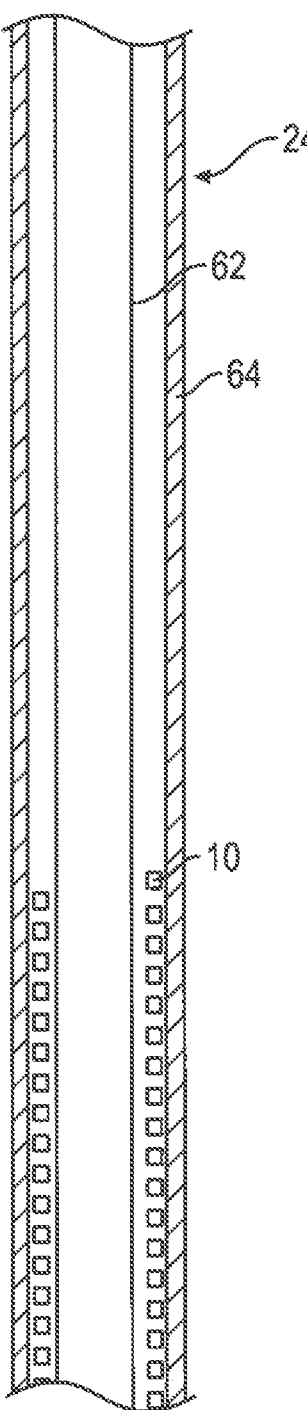
FIG. 2 is a sectional view of a release device with the intraluminal device mounted therein.
Figure 3:
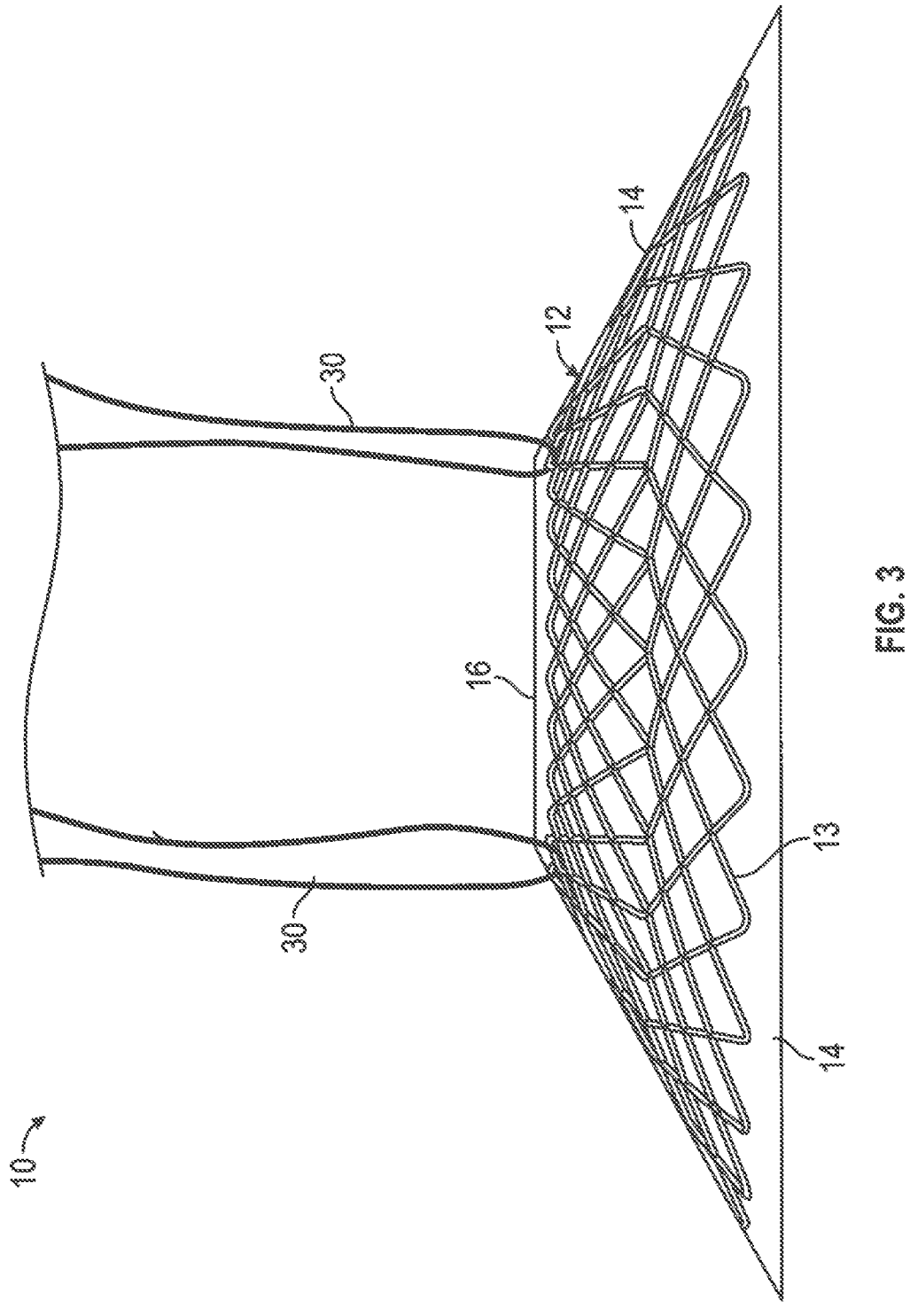
FIG. 3 is a medial elevational view of an intraluminal device.
Figure 4:
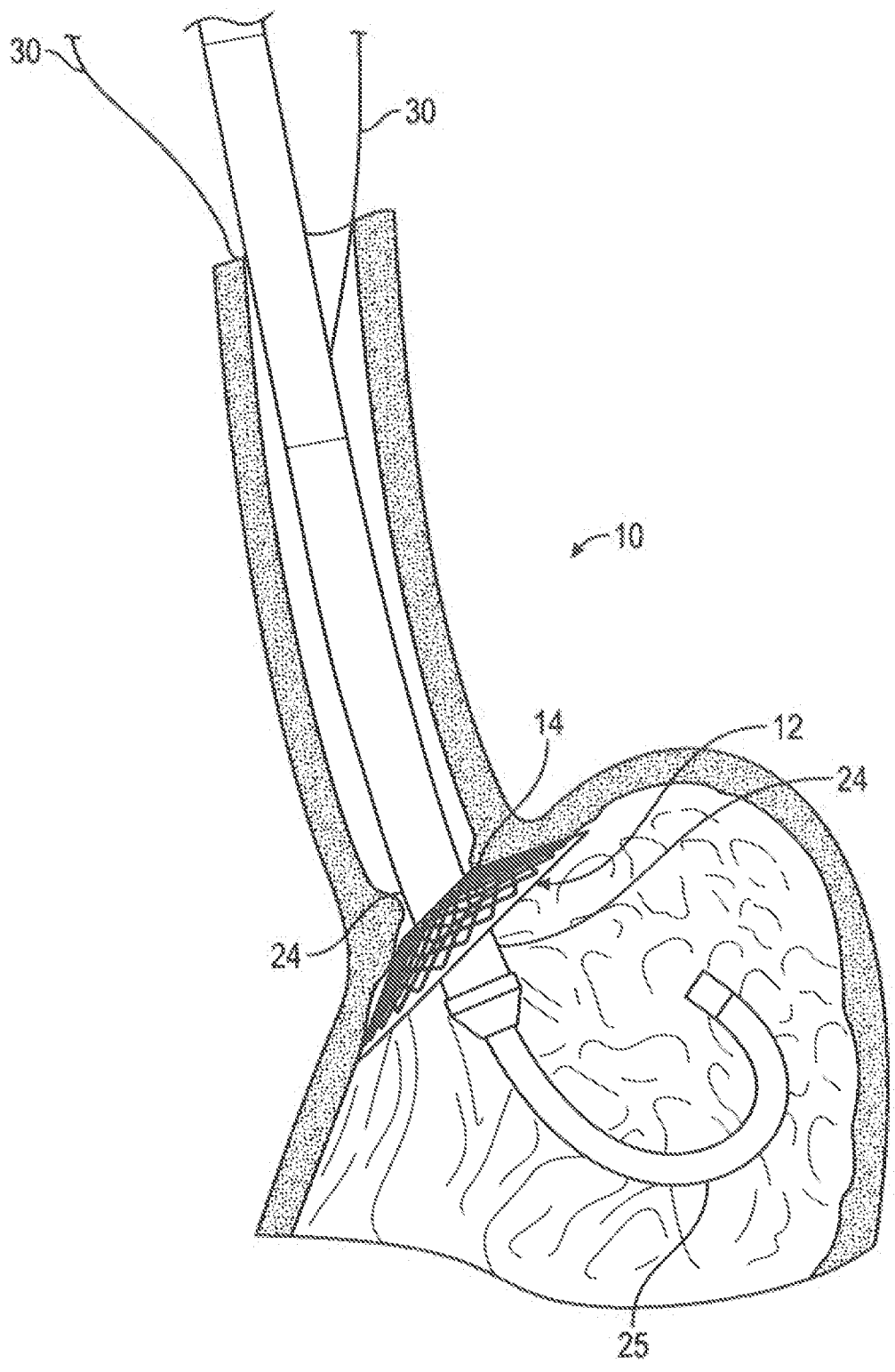
FIG. 4 medial elevational view illustrating positioning of the intraluminal device for attachment.

Method 9 begins by providing laparoscopic access, such as by incision, between the stomach and the diaphragm and insufflating the abdomen at 17 (FIG. 11). Also, a visualization device, such as an endoscope 25 is trans-orally deployed to the stomach and a deployment device 24 is deployed to the stomach either over the endoscope or adjacent the endoscope (FIG. 4). As seen in FIG. 2, the intraluminal device 10 may be compressed between an inner tube 62 and an outer tube 64 of deployment device 24. Intraluminal device 10 is deployed in the stomach at 18 by proximal movement of outer tube 64 with respect to inner tube 62 which allows the intraluminal device to self-expand into its use configuration in the stomach. The stomach is insufflated using the endoscope and the endoscope is retroflexed as seen in FIG. 4 in order to visualize the intraluminal device during affixation. Endoscope 25 and deployment device 24 may each be a manual instruments that are manipulated by a surgeon or may be an end-of-arm tools that are manipulated by a surgical robot of the type that is commercially available from multiple sources.

Deployment device 24, whose outer diameter is less than the diameter of opening, or open portion 16, is then positioned at 20 with its outer tube 64 within opening 16 while a proximal force is placed on retention filaments 30 which are looped around a proximal portion of the intraluminal device and extend out of the patient's mouth. The proximal force applied to the retention filaments brings intraluminal device 12 into contact with the cardiac portion of the stomach. Since the deployment device is positioned in the esophagus it generally aligns opening 16 with the GE junction so that ingested food passes through opening 16 not between wall 12 and the stomach wall. Such general alignment is also maintained with the deployment device during fastening of the intraluminal device to the stomach wall at 34.

Intraluminal device 10 is fastened at 34 from the abdominal cavity with at least one laparoscopic instrument 11, such as a laparoscopic needle or other fastening device, while visualizing the intraluminal device with endoscope 25 from within the stomach while it is being fastened at 34. The visualizing of the interaction between the laparoscopic instrument and the intraluminal device in the stomach guides further movement between the fastening device and the intraluminal device in order to properly carry out optimal fastening of the intraluminal device to the cardiac portion of the stomach. For example, if used with a surgical robot, one robot arm could operate laparoscopic instrument 11 in the form of an end of arm tool. Another robot arm could operate endoscope 25 as an end of arm tool. Images captured by the endoscope in the stomach could then be used by a common robot controller to guide movement of laparoscopic instrument 11 in order to endure proper engagement between attachment fasteners and the intraluminal device.

Figures 5, 5A:
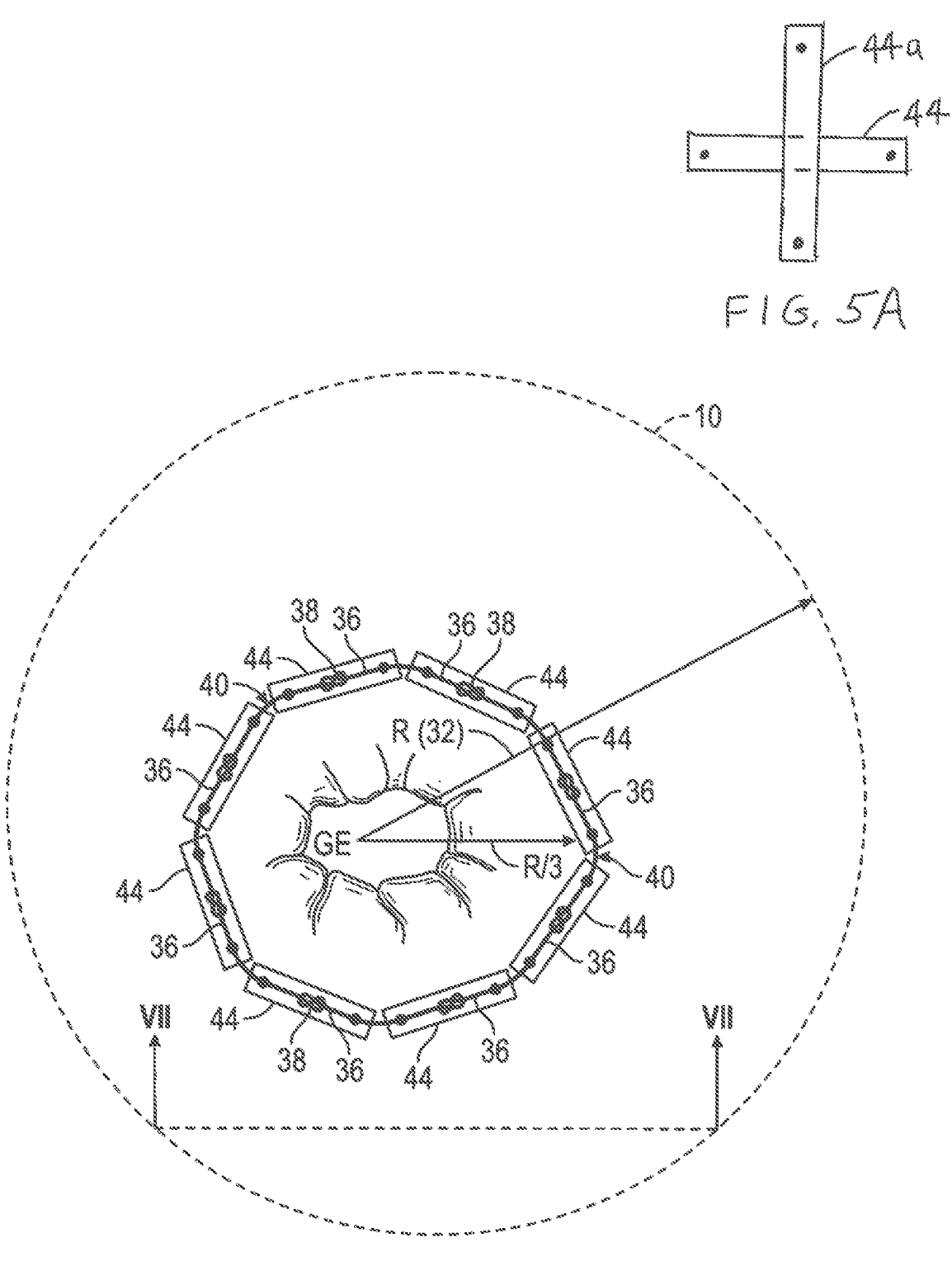
FIG. 5 is a sectional view taken along the lines V-V in FIG. 1.
FIG. 5A is an enlarged plan view of an alternative embodiment of a reinforcing device.
Figure 6:
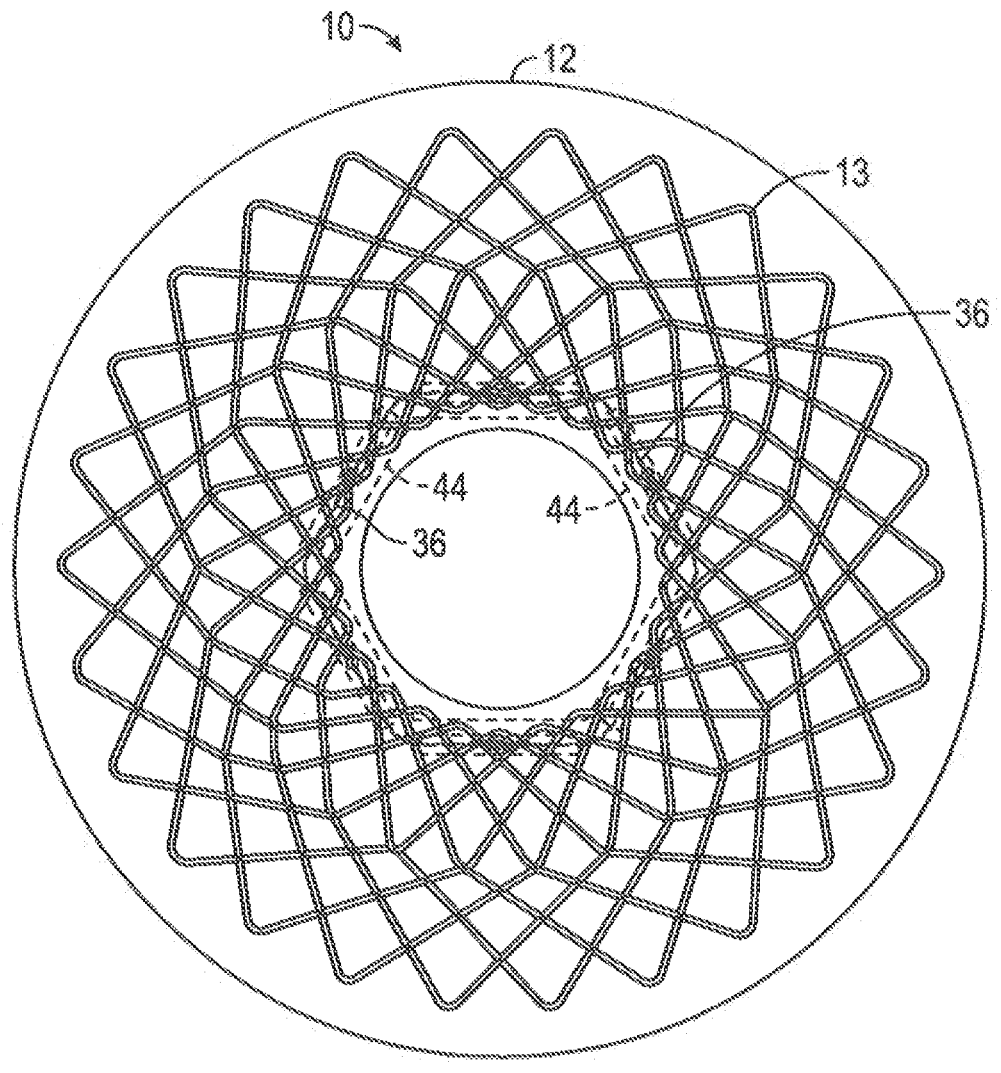
FIG. 6 is a sectional view taken along the lines VI-VI in FIG. 1.

In the illustrated embodiment, the fastening is with sutures in the form of individual strands 36 that are arranged a generally circular pattern around the esophagus, which is generally aligned with opening 16 by release device 24, as best seen in FIGS. 4 and 5. Each suture strand is applied over a reinforcement, such as a pledgett 44, between the suture strand and the outer stomach wall. The suturing device causes the suture loop to penetrate the reinforcement 44, pass through the stomach wall as well as wall 12 of intraluminal device 10. The suture loop then directed to straddle around a structural member 13 of wall 12 and then back through wall 12, the wall of the stomach and through the reinforcement 44 under guidance from visualization with endoscope 25. The suture loop is then tied off thus forming a knot 38 using conventional techniques. All of this fastening is visualized from within the stomach using endoscope 25. The laparoscopic fastening device may be a conventional instrument that is manipulated by a surgeon or may be an end-of-arm tool that is manipulated by a surgical robot of the type that is commercially available from multiple sources.

Figure 7:
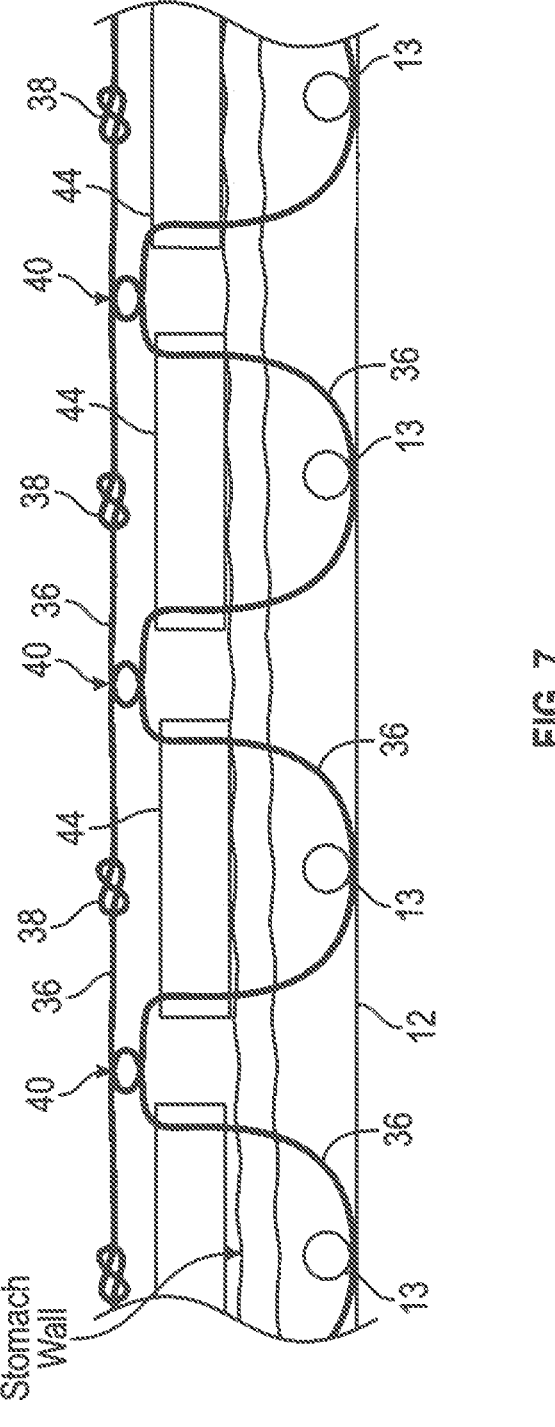
FIG. 7 is a sectional view taken along the lines VII-VII in FIG. 5.
Figure 8A:
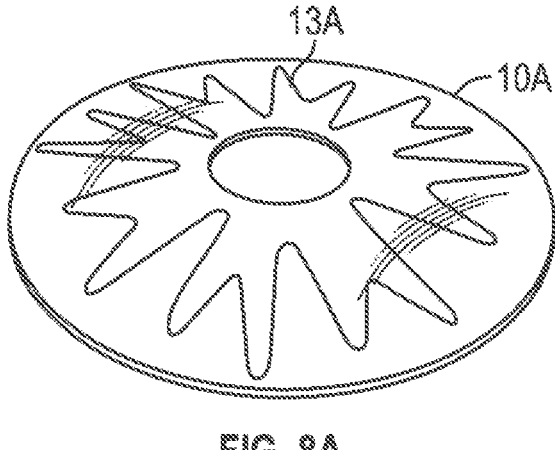
FIG. 8A-8E are perspective views of alternative embodiments of an intraluminal device.
Figure 8B:
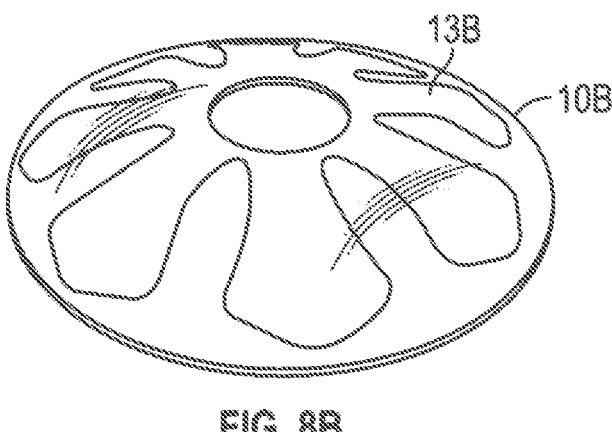
Figure 8C:
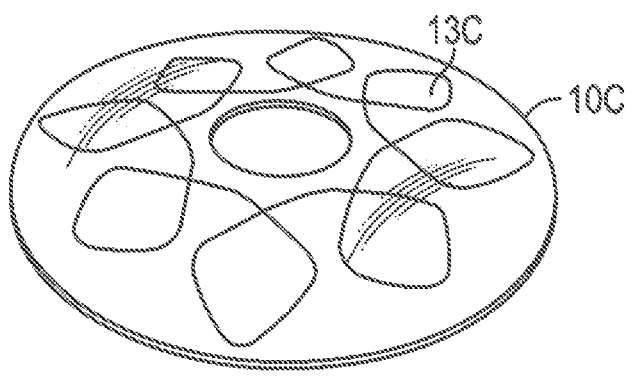
Figure 8D:
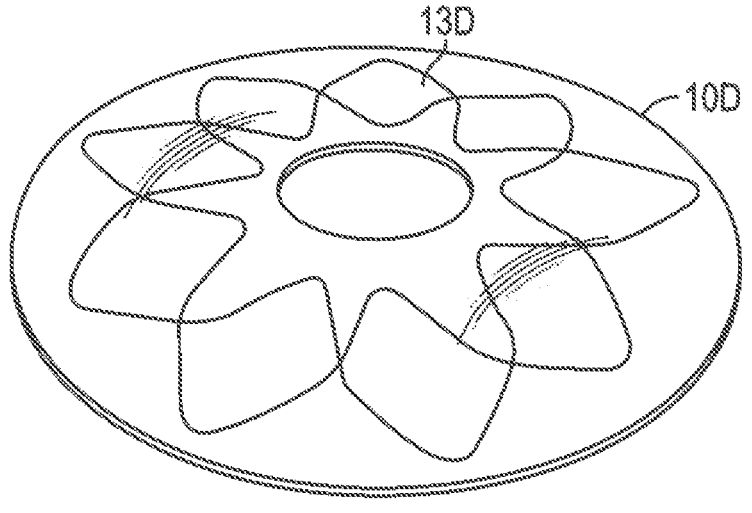
Figure 8E:
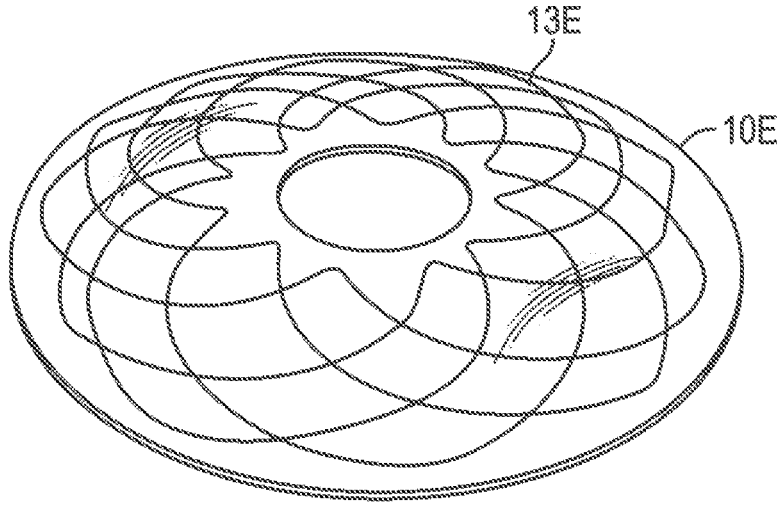

A reinforcement in the form of a radial restraint 40 is applied to the suture strands 36 in order avoid the suture material of the strands cutting through the stomach wall and releasing the fastening of the device. Such radial constraint 40 could be applied by interweaving, or overlapping, the strands of adjacent loops 36, as best seen in FIGS. 5 and 7 so that one strand applies radial restraint to the adjacent strand and vice versa. Alternatively, radial restraint 40 could be applied by each reinforcement 44 being formed with an integral structural reinforcement in order to resist cutting of the reinforcement by the strands of suture loops 36.

Alternatively, or additionally, the reinforcement may be provided by the production of scar material, such as collagen, in the stomach tissue contacted by a pledget 44. This occurs in the illustrated embodiment, by making pledget 44 from a biologically absorbable, or re-sorbable, material of the type known in the art. Such scar material is formed concurrently with and as a result of the biological absorption of the absorbable material making up pledget 44. In the illustrated embodiment, suture stands 36 are non-absorbable. This allows intraluminal device 10 to be deployed for an extended period of time without losing strength of fastening over time from an absorbable suture. Pledget 44 may be made from multiple layers, each having a different rate of absorption. The layer with the highest rate of absorption could be positioned against the stomach wall and other layer(s) further away. The provision of an absorbable pledget thus provides two functions. It is absorbed by the patient so no laparoscopic access is needed to remove the pledget after use. Since the absorption of the reinforcement causes the formation of collagen or scar material, some reinforcement against penetration of the stomach tissue by the suture strands remains, even after the reinforcement is absorbed. However, after being severed in the stomach, the entire non-absorbed suture can be retracted to the stomach because its knots can pull through the collage in in the stomach wall.

Explantation of intraluminal device at 68, such as after weeks or months of use, or longer, as will be described in more detail below. The suture strands 36 are severed in the stomach such as with an endoscopically deployed scissors and knots 38 pulled through the stomach wall into the stomach to allow the suture strands to be removed endoscopically or pass through the intestines. While the knot would resist being pulled through a reinforcement made from a rigid material, the absorbable reinforcement should be at least mostly absorbed by the time of explantation, and replaced with scar tissue. Knots 38 can be pulled through such scar tissue yet the scar tissue is sufficiently rigid to provide reinforcement to the suture strand to resist their cutting of stomach tissue. Since the pledget 44 will have been all or mostly absorbed by the time of explantation of device 10, the device and all other components such as suture strands, can be removed endoscopically from the stomach. Therefore, no portion of the implanted device will remain behind in the patient after explanation and the explantation does not require any invasive procedure such as laparoscopic incisions. Alternatively, or additionally, radial reinforcement 40 could include making the pledget 44 with an adherence surface feature that abuts the outer surface of the stomach that causes adherence between the restraint and the stomach. That adherence further strengthens the reinforcement in order to resist buckling. The surface of the reinforcement facing away from the stomach may have a non-adherence surface to avoid adhesion with other surfaces in the abdomen.

While intraluminal device 10 is being fastening such as by suturing, a fold of stomach tissue may be made to wrap at least partially around pledget 44. An additional pledget 44*a* may be positioned in a traversing fashion over pledget 44 as shown in FIG. 5A. Transverse pledget 44*a* may be affixed more loosely than pledget 44 in order to provide additional support yet allow lateral movement of pledget 44. With a tissue fold at least partially wrapped around pledget 44, the placement of transverse pledget 44*a* provides the tissue fold to be sandwiched between two bio-absorbant pledgets 44, 44*a*. This further strengthens the tissue fold as additional collagen or scar material will form.

The severing of suture strands 36, such as with an endoscopic scissors or the like, may be conveniently performed where the suture material crosses the structural member or members 13 thus spacing the suture material from the wall of device 10. The suture loops could be removed from the patient endoscopically or left in place loosely in the stomach to be passed on by peristalsis. The intraluminal device is removed trans-orally. The openings in the stomach wall left by the suture strands will heal. Wall 12 may include an involute collar or ring around opening 16 to provide additional stiffness to wall 12 and may be large enough to capture suture loops 36. While the fastening of intraluminal device 10 is illustrated using a laparoscopic needles to apply sutures, other laparoscopic fastening techniques could be used such as applying mechanical fasteners from the abdomen.

Wall 12 of device 10 in the illustrated embodiment has a generally circular shaped circumference but may have any shape that is conformable with the cardiac portion of the stomach. For example, although as shown as circular or elliptical, device 10 could have a flower-pedal shape, or the like. Wall 12 has a mean radius 32 measured from the center of opening 16 to the outer edge. Suture loops 36 are positioned within the half of radius 32 that is closest to opening 16. The suture loops may be within the third of the radius closest to said opening and may even be within the quarter of radius 32 closest to opening 16. This is advantageous because the portion of the stomach closest to the esophagus experiences the least amount of peristalsis because the portion of the stomach at the esophagus does not substantially move. So fastening wall 12 close to opening 16 minimizes movement of the sutures in response to peristalsis of the stomach.

Figure 9:
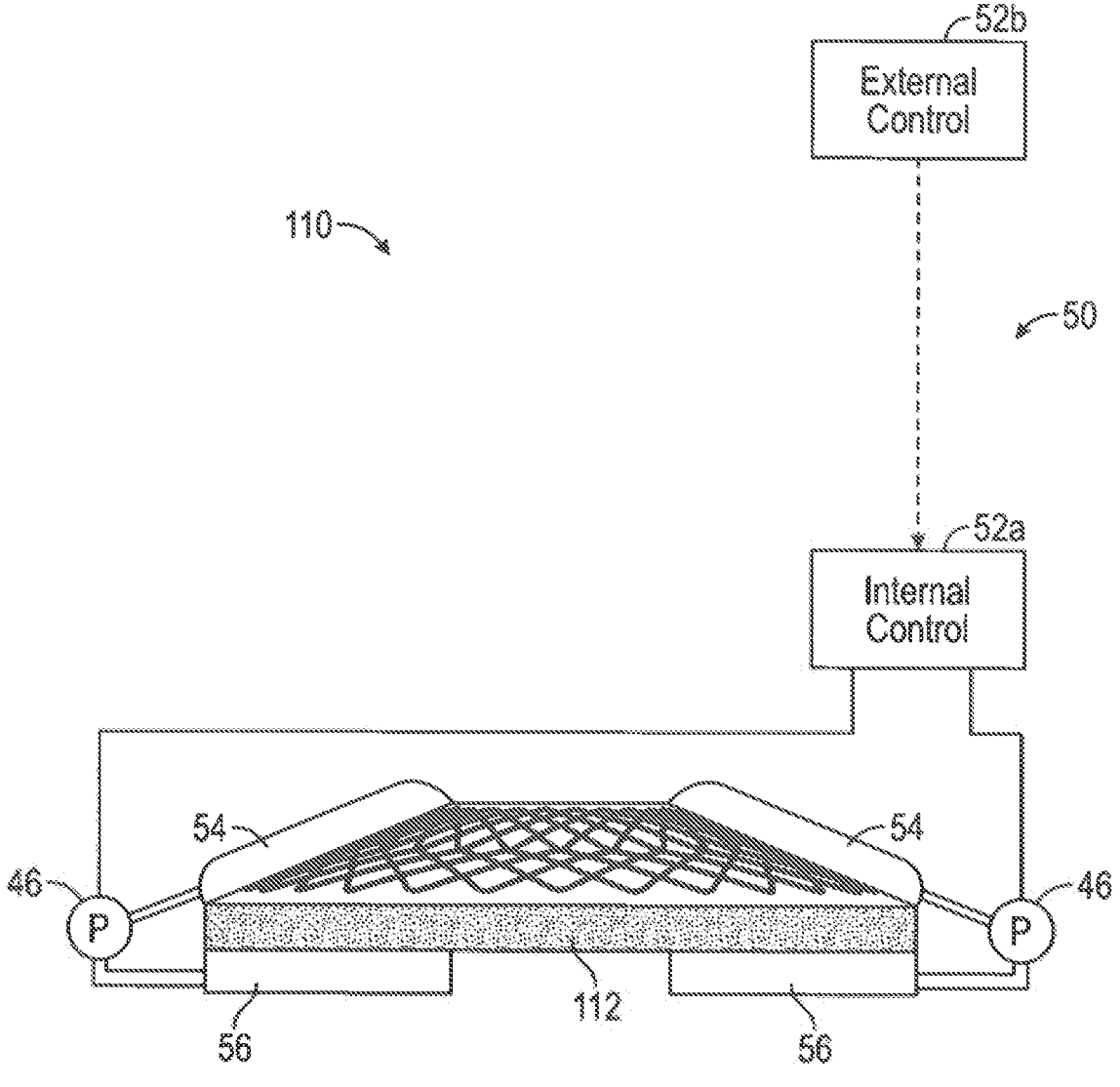
FIG. 9 is a median elevational view of an adjustable embodiment of an intraluminal device.

In an alternative embodiment, an intraluminal device 110 is able to adjust stress applied to the cardiac portion of the stomach. Referring to FIG. 9, intraluminal device 110 includes a control 50 that has an internal module 52*a* implanted in the patient to adjust amount of stress applied by device 110. Control 50 may further include an external module 52*b* that his external the patient and communicable with the internal module 52*a* such as by radio frequency wireless communication. External module 52*b* may have a user interface (not shown) for operation by the user or a practitioner. Device 110 may further have at least one bladder 54 between wall 112 and the cardiac portion of the stomach in fluid communication with at least one bladder 56 via a pump 46 that is controlled by internal control 52*a*. Stress can be adjusted by pumping fluid between bladder 54 and bladder 56. Instead of an electronic control, bladder(s)

52a may be connected with a port at the patient's skin surface for inflation or deflation via an external bladder or pump.

Figure 10:
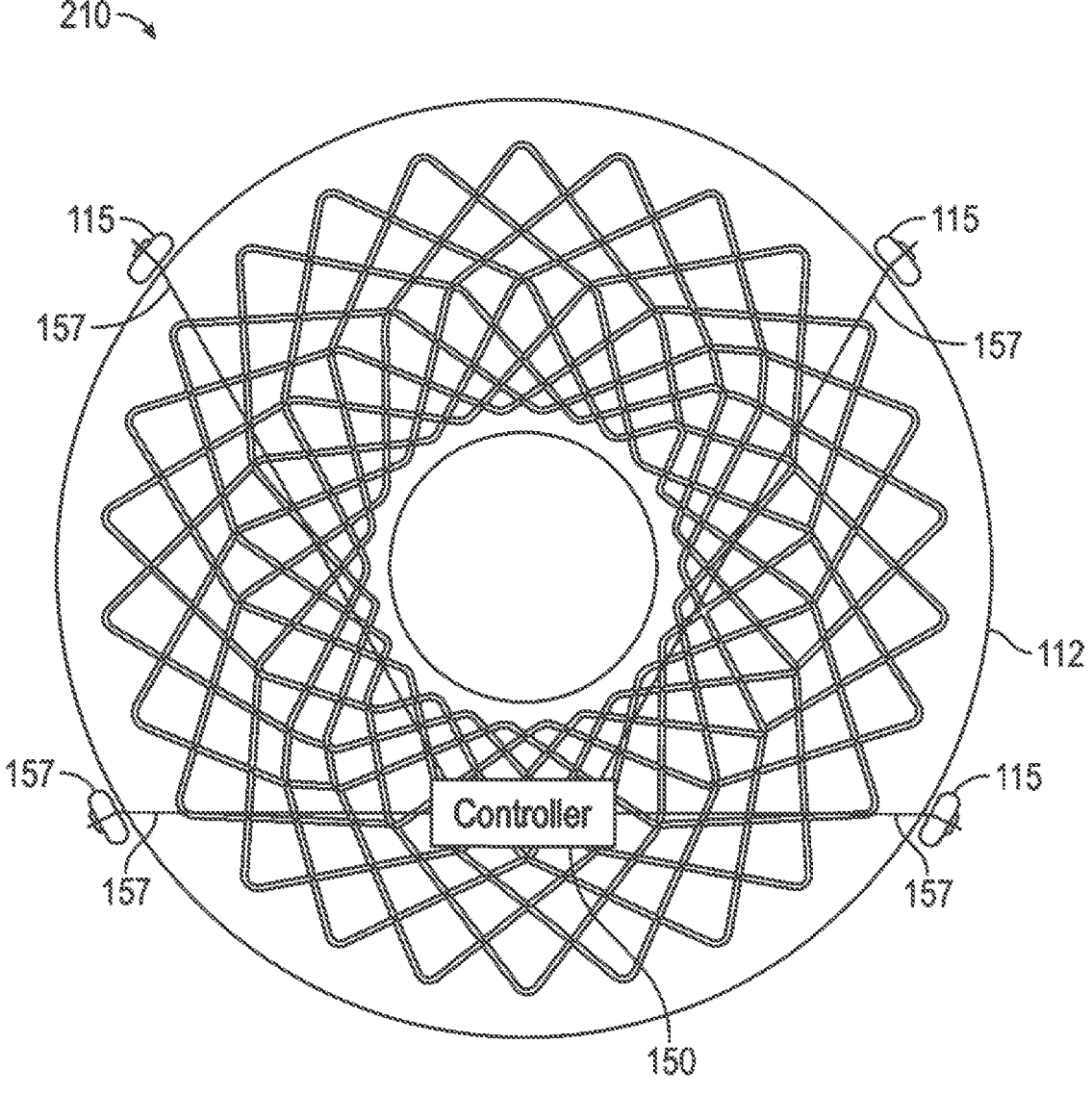
FIG. 10 is a bottom plan view of another adjustable embodiment of an intraluminal device.
Figure 12:
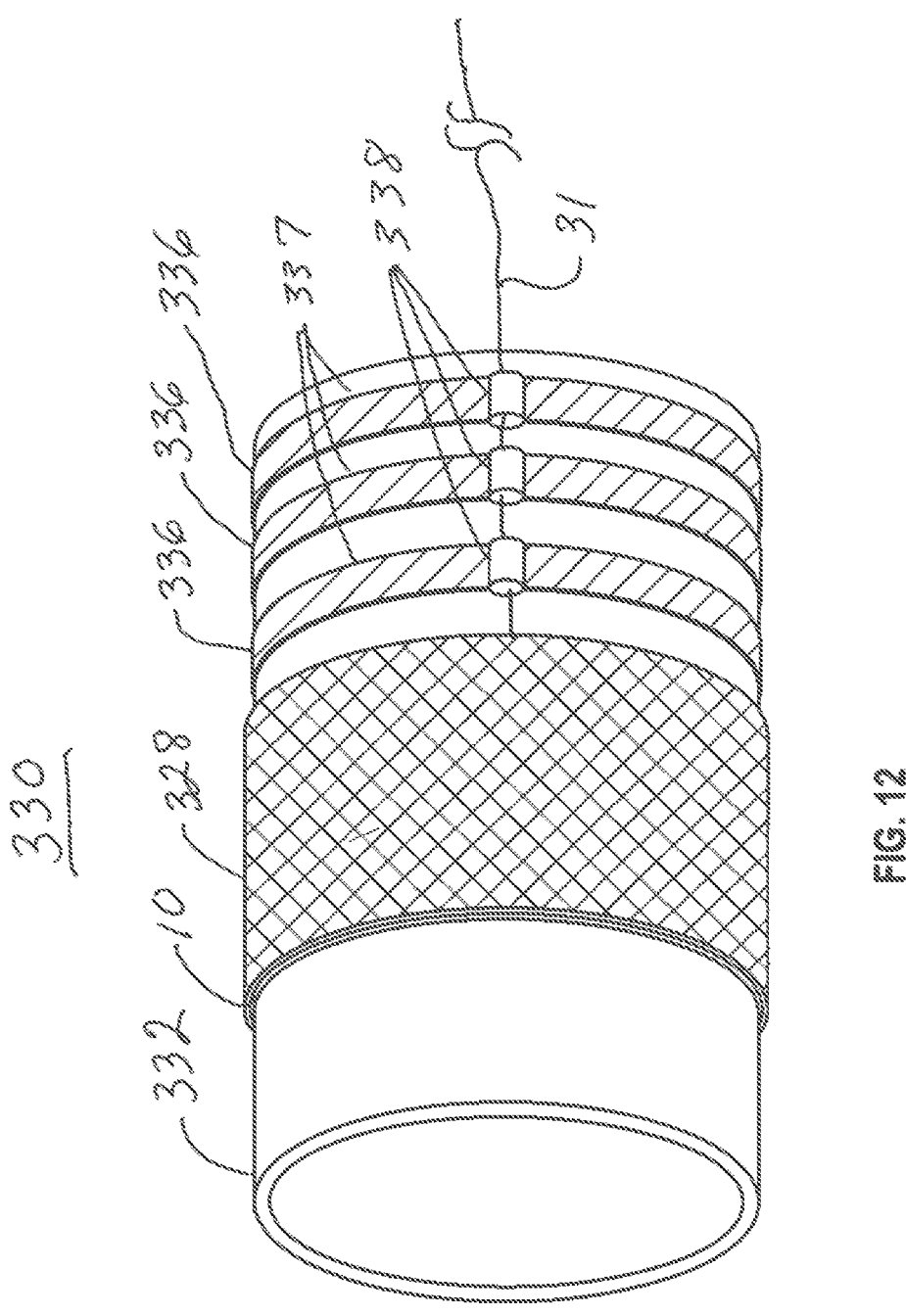
FIG. 12 is a perspective view of a kit that is adapted for use with an endoscope to convert the endoscope into a combination endoscope and intraluminal device deploying device.

In another alternative embodiment, an intraluminal device 210 is able to adjust stress applied to the cardiac portion of the stomach. Referring to FIG. 10, intraluminal device 210 includes a control 150 that is interconnected to various portions of wall 112 by filaments 157 connected to the wall with fasteners 115. By adjusting the length of filaments 157, control 150 may reduce or increase the surface area of surface 114 in contact with the cardiac portion of the stomach to adjust the applied stress. This may be facilitated by configuring wall 112 with leaves or flower pedals (not shown) that are each connected with one filament 157 to reduce the amount of force required to change the surface area in contact with the cardiac portion of the stomach. While not shown in FIG. 10, controller 150 may have an external and internal control module as previously described. The inclusion of leaves may also make the intraluminal device more adaptable to various applications. For example, it may be applied to patients having an altered anatomy with the leaves useful for adapting to the anatomy of the patient.

The ability to adjust amount of stress applied by the intraluminal device allows the amount of satiety to be optimized to achieve desired weight loss. This may be accomplished by providing feedback to controller 150 of, for example, amount of weight loss. Controller 150 may then adjust mount of stress in order to optimize amount of satiety provided by the stress level.

FIGS. 8A through 8E show various configurations of intraluminal devices 10A-10E with configurations of structural members 13A-13E. Other configurations are possible. For example, segments of the structural members may be denser proximal the open portion of the intraluminal device than distal thereto. This increases the likelihood that suture strands will engage a structural member when the stands are placed closer to the opening.

Other variations in the intraluminal device may be provided. For example, at least one magnet may be provided on the wall of the device that is used to fasten the device to the cardiac portion of the stomach by engaging at least one magnet positioned in the abdominal cavity of the patient. Alternatively, the wall or the intraluminal device may be no larger than required to engage with the suture loops in the stomach, such as a narrow ring shape or the like. While such configuration may not provide as much stimulus of the baroreceptors in the cardiac portion of the stomach, it may provide sufficient stimulus of the receptors. Intraluminal device 10, 110, 210 may have various uses. The intraluminal device may be used as a bariatric device. The intraluminal device may be used to treat a metabolic disease. Because the intraluminal device resists upward movement to the stomach wall it may be used to treat gastric reflux disease or hiatal hernia.

Figure 13:
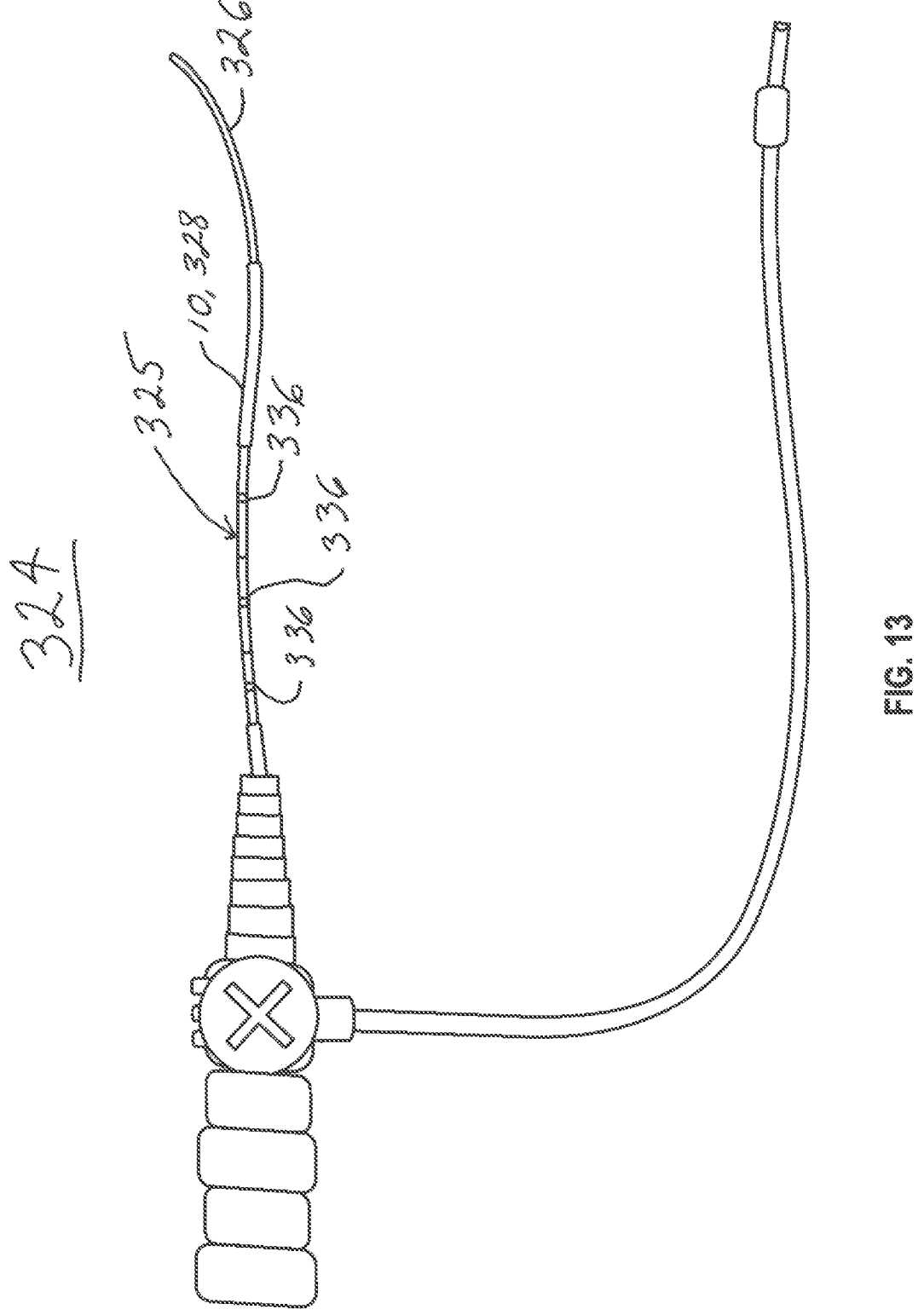
FIG. 13 is perspective view of a combination endoscope and intraluminal device deploying device.

In an alternative embodiment illustrated in FIGS. 12-15, the endoscope and deployment device are combined in a combination endoscope and deployment device 324. As best illustrated in FIG. 13, combination endoscope and deployment device 324 includes the intraluminal device 10 positioned at an exterior surface of shaft 325 of the endoscope. A distal end portion 326 of endoscope shaft 325 includes a steerable portion 326 that can be retroflexed to visualize intraluminal device 10 during fastening to the cardiac portion of the stomach. Intraluminal device wall 12 is a self-expandable wall that is compressed to endoscope shaft 325. A compression device 238 keeps self-expandable wall 12 compressed to endoscope shaft 325. Compression device 238 may be a sleeve over the intraluminal device, filament wrapped over intraluminal device wall 12, or the like. A deploying filament 31 extends from compression device 328 through the esophagus to external the patient where it can be manipulated by the surgeon or surgical robot. The deploying filament is adapted to release compression device 328 to allow intraluminal device 10 to self-expand in the patient's stomach. For example, if compression device 328 is a sleeve, it may be made with a series of openings so that a proximal force from the deploying filament will distort the sleeve to have an increase diameter to allow it to be slid off the intraluminal device. If compression device 328 is a filament wrapped over intraluminal device 10, the deploying filament may be an extension of the wrapped filament so that a proximal force from the deploying filament will remove the wrapped filament to allow the intraluminal device wall to self-expand.

Figure 14:
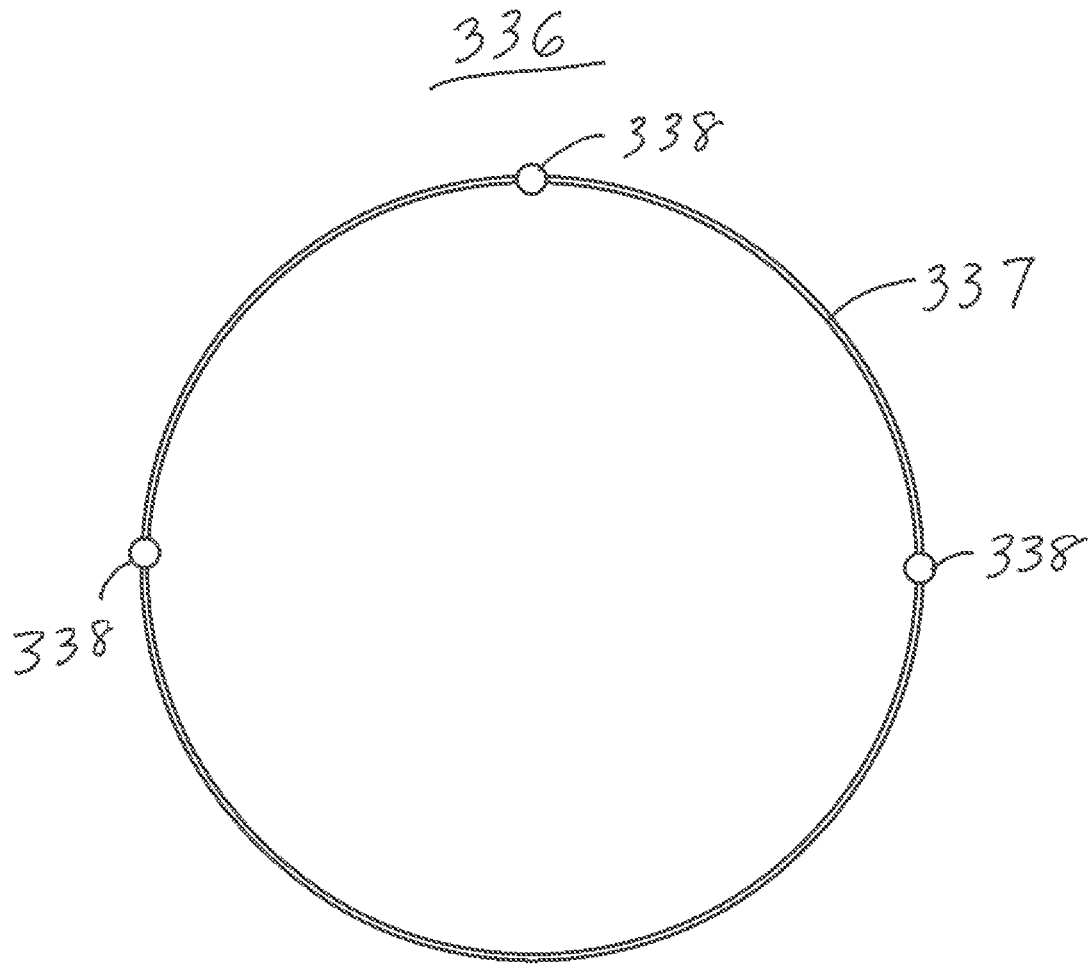
FIG. 14 is an end elevational view of a filament guide.

Combination endoscope and deployment device 324 includes at least one filament guide 336 positioned on endoscope shaft 333 positioned proximal to intraluminal device 10 and adapted to guide movement of deploying filament 31. Filament guide 336 may also guide movement of retaining filaments 30. As best illustrated in FIG. 14, filament guide 336 includes a circular band 337 that can grip shaft 325 to stay in a stationary position. Filament guide 336 includes one or more guide channels 338 integral with band 337. Each guide channel 338 is for guiding movement of a retaining or a deploying filament 30, 31. In the illustrated embodiment, a plurality of filament guides 336 are spaced along shaft 325.

While combination endoscope and deployment device 324 may be supplied compete in the configuration illustrated in FIG. 13, for example as a single-use device, a kit 330 may be provide to convert a conventional endoscope to a combination endoscope and deployment device. Kit 330 includes a holder 332 having an inner diameter that is larger than the outer diameter of the shaft of said endoscope. For example, when used with a conventional endoscope having an outer diameter of from 0.9 to 1.0 cm, holder 332 may have an inner diameter of 1.2 cm. Intraluminal device 10 is compress on holder 332 by a compression device 328 made up of a sleeve or a wrapped filament over intraluminal device 10 and adapted to keep device wall 12 compressed to the holder with deploying filament 32. Kit 330 may further include at least one filament guide 336 positioned on the holder and adapted to guide movement of the deploying filament 31. Kit 330 may further includes one or more retention filaments 30 adapted to extend from the intraluminal device to external the patient, with the filament guide adapted to guide movement of the retention filaments.

Figure 15:
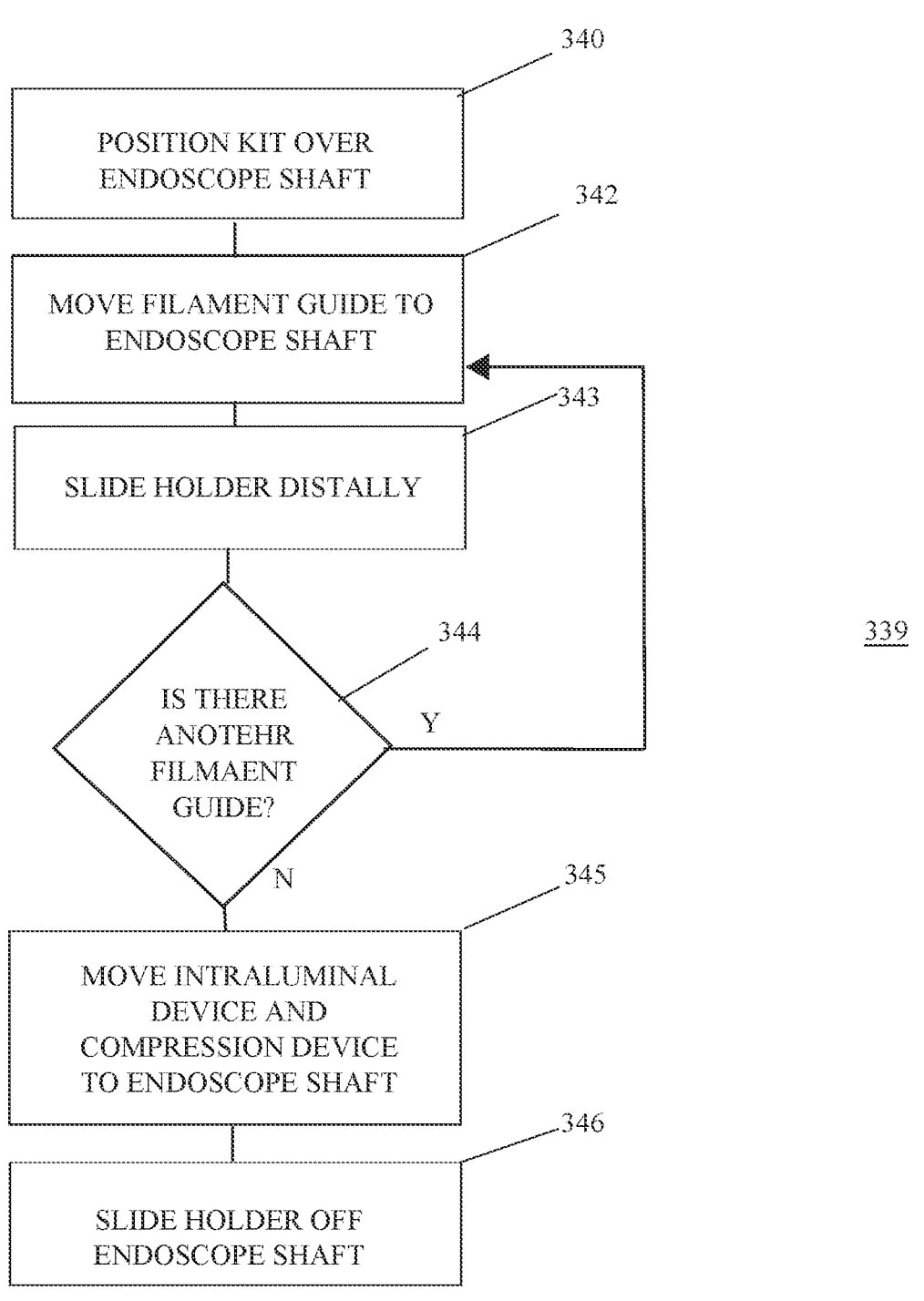
FIG. 15 is a block diagram of a method of converting an endoscope into a combination endoscope and intraluminal device deploying device.

A method 339 of converting an endoscope to a combination endoscope and intraluminal device is illustrated in FIG. 15. Method 339 begins at 340 by positioning kit 330 over the shaft 325 of the endoscope with filament guides 336 proximal intraluminal device 10 and compression device 328. A first filament guide is moved to the endoscope shaft at 342 by sliding the guide off of the holder and contracting to the endoscope shaft 325. The holder is then slid distally along the endoscope at 342. If another filament guide remains on the holder (344), steps 342 and 343 are repeated. If not, the intraluminal device and compression device are moved from the holder to the endoscope shaft at 345 by sliding both off the holder where they will compress further to grip the shaft. The holder is then slid off the endoscope shaft at 346 to complete the method.

The filament guides and compression device may be removed from the endoscope shaft after the intraluminal device is affixed to the patient by reversing method 339. Alternatively, holder 332 could be retained to the endoscope's shaft during use so that it is available for use to remove kit 330 after the intraluminal device is deployed. This may be accomplished by having friction members, such as wide bands, extending from one or both end of holder 332 to grip the shaft, other variations will be apparent to the skilled artisan.

Figure 16:
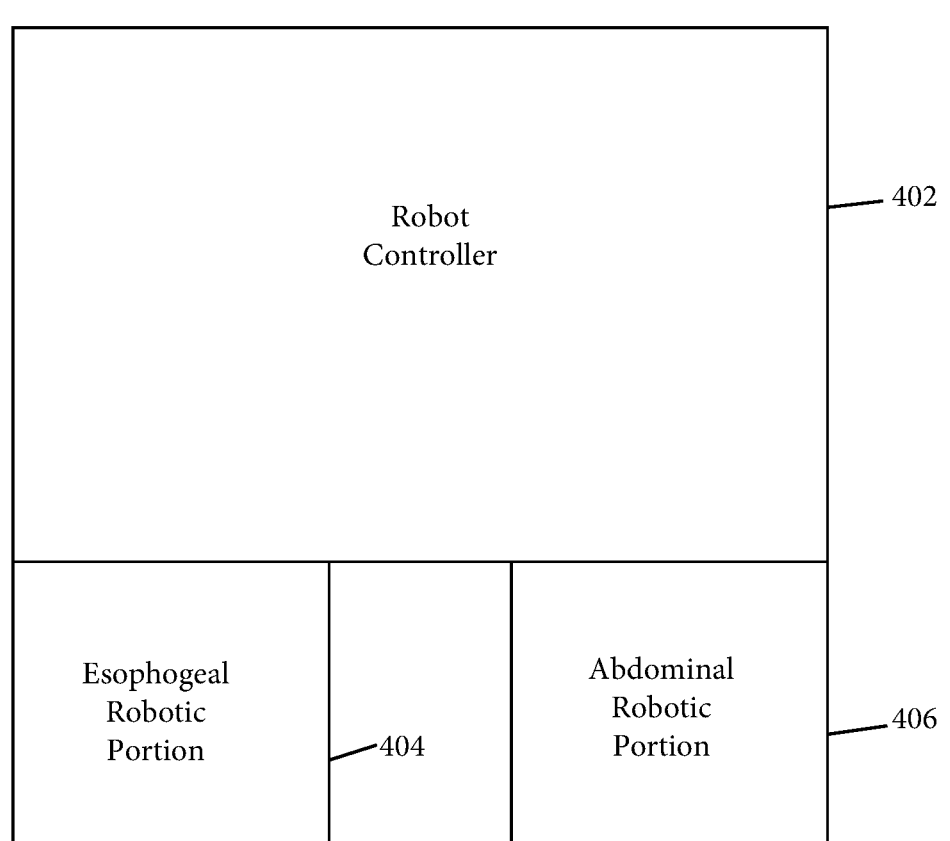
FIG. 16 is a block diagram of an intraluminal system that is adapted to deploy an intraluminal device to the cardiac region of the stomach.

Illustrated in FIG. 16 is a surgical robotic system 400 that is useful in carrying out the intention. Robotic system 400 has an esophageal robotic portion end-of-arm tool 404 that both deploys the intraluminal device in the stomach and visualizes the intraluminal device while it is being fastened. Robotic system 400 further has an abdominal robotic portion 406 that carries out fastening of the intraluminal device to the cardiac portion of the stomach from the abdominal cavity. A robotic control 402 adjusts the relative position between tools 404 and 406 to ensure that the intraluminal device is properly engaged by the fasteners and that the anatomy of the patient is not compromised by the deployment process.

Changes and modifications in the specifically described embodiments can be carried out without departing from the principles of the present invention which is intended to be limited only by the scope of the appended claims, as interpreted according to the principles of patent law including the doctrine of equivalents.

The embodiments of the invention in which an exclusive property or privilege is claimed are defined as follows:

1. A method of deploying an intraluminal device to the cardiac region of the stomach, the device comprising a wall defining a surface and an open portion said wall that is alignable with the gastroesophageal (GE) junction, said surface and the cardiac portion of the stomach conformable with each other, said method comprising:

deploying the intraluminal device trans-orally to the stomach;

retaining the intraluminal device in the stomach in contact with the cardiac portion of the stomach with the open portion generally aligned with the GE junction;

fastening the retained intraluminal device to the cardiac portion of the stomach through a wall of the stomach from within the abdominal cavity with at least one laparoscopic instrument;

visualizing the intraluminal device within the stomach with an endoscope during the fastening, wherein said fastening comprises suturing with suture strands and reinforcing the suture strands at the abdominal side of each suture strand wherein said reinforcing comprises producing scar material in the stomach tissue contacted by the suture strand; and explanting the intraluminal device by severing the suture strands in the stomach and pulling the knots of the severed suture strands through the stomach wall into the stomach.

2. The method as claimed in claim 1 wherein said deploying comprises deploying the intraluminal device from a deployment device in the stomach and said retaining the intraluminal device comprises positioning the deployment device within the open portion of the wall in order to generally align the open portion with the GE junction.

3. The method as claimed in claim 2 wherein said retaining the device further comprises applying a proximal force on at least one retention filament connected with the wall and the retention filament passing through the esophagus.

4. The method as claim in claim 1 wherein said deployment device comprises said intraluminal device position at an exterior surface of the endoscope.

5. The method as claimed in claim 1 wherein said reinforcing further comprises providing radial restraint to the suture strands.

6. The method as claimed in claim 5 wherein said providing radial restraint comprises engaging adjacent suture strands with each other.

7. The method as claimed in claim 1 wherein said producing scar material comprises positioning a biologically absorbable material between the suture strand and the stomach tissue.

8. The method as claimed in claim 7 wherein said suture stands are made from a non-absorbable material.

9. The method as claimed in claim 7 wherein said biologically absorbable material comprises multiple layers, each having a different rate of absorption.

10. The method as claimed in claim 9 wherein the layer with a highest rate of absorption is positioned against the stomach wall.

11. The method as claimed in claim 7 wherein said biologically absorbable material including a structural component that resists warping.

12. The method as claimed in claim 9 wherein the one of said layers furthest from the stomach tissue having an outer surface that is adapted to resist adhering to another surface.

13. The method as claimed in claim 1 wherein said intraluminal device has a plurality of structural members and has a higher density of said structural members proximal said opening than distal said opening.

14. The method as claimed in claim 1 wherein said intraluminal device is made at least in part from a bio-absorbable material.

15. The method as claimed in claim 1 wherein said wall includes an involute collar around said open portion.

16. The method as claimed in claim 1 wherein fastening the intraluminal device to the cardiac portion of the stomach from within the abdominal cavity comprises looping a suture strand around a structural member of the intraluminal device.

17. The method as claimed in claim 1 wherein said intraluminal device is used to treat at least one chosen from obesity, a metabolic disease, gastric reflux and hiatal hernia.

18. The method as claimed in claim 1 wherein said explanting the intraluminal device further including withdrawing the intraluminal device through the esophagus.

\* \* \* \* \*